US008691567B2

(12) United States Patent
Harper et al.

(10) Patent No.: US 8,691,567 B2
(45) Date of Patent: Apr. 8, 2014

(54) ALTERNATIVE EXPORT PATHWAYS FOR VECTOR EXPRESSED RNA INTERFERENCE

(75) Inventors: Scott Harper, Iowa City, IA (US); Beverly L. Davidson, Iowa City, IA (US)

(73) Assignee: University of Iowa Research Foundation, Iowa City, IA (US)

(*) Notice: Subject to any disclaimer, the term of this patent is extended or adjusted under 35 U.S.C. 154(b) by 0 days.

(21) Appl. No.: 13/529,925

(22) Filed: Jun. 21, 2012

(65) Prior Publication Data

US 2012/0270317 A1 Oct. 25, 2012

Related U.S. Application Data

(62) Division of application No. 12/515,717, filed as application No. PCT/US2007/085789 on Nov. 28, 2007, now Pat. No. 8,227,592.

(60) Provisional application No. 60/861,500, filed on Nov. 29, 2006, provisional application No. 60/861,819, filed on Nov. 30, 2006.

(51) Int. Cl.
*C12N 15/85* (2006.01)
*C07H 21/02* (2006.01)
*C07H 21/04* (2006.01)

(52) U.S. Cl.
USPC .................. 435/325; 536/23.1; 536/24.5

(58) Field of Classification Search
None
See application file for complete search history.

(56) References Cited

U.S. PATENT DOCUMENTS

| | | | |
|---|---|---|---|
| 4,683,202 | A | 7/1987 | Mullis |
| 5,880,276 | A | 3/1999 | Hammarskjold et al. |
| 5,928,906 | A | 7/1999 | Koster et al. |
| 7,902,352 | B2 | 3/2011 | Kaemmerer et al. |
| 8,227,592 | B2 | 7/2012 | Harper et al. |
| 8,258,286 | B2 | 9/2012 | Davidson et al. |
| 2004/0023390 | A1 | 2/2004 | Davidson et al. |
| 2004/0241854 | A1 | 12/2004 | Davidson et al. |
| 2005/0042646 | A1 | 2/2005 | Davidson et al. |
| 2005/0106731 | A1 | 5/2005 | Davidson et al. |
| 2005/0255086 | A1 | 11/2005 | Davidson et al. |
| 2006/0009408 | A1 | 1/2006 | Davidson et al. |
| 2006/0257912 | A1 | 11/2006 | Kaemmerer et al. |
| 2008/0176812 | A1 | 7/2008 | Davidson et al. |
| 2008/0274989 | A1 | 11/2008 | Davidson et al. |
| 2009/0036395 | A1 | 2/2009 | Davidson et al. |
| 2009/0105169 | A1 | 4/2009 | Davidson et al. |
| 2009/0130751 | A1 | 5/2009 | Davidson et al. |
| 2010/0008981 | A1 | 1/2010 | Kaemmerer et al. |
| 2010/0144026 | A1 | 6/2010 | Davidson et al. |
| 2010/0190243 | A1 | 7/2010 | Davidson et al. |
| 2010/0325746 | A9 | 12/2010 | Kaemmerer et al. |
| 2011/0111491 | A1 | 5/2011 | Davidson et al. |
| 2011/0212520 | A1 | 9/2011 | Davidson et al. |
| 2011/0244561 | A1 | 10/2011 | Davidson et al. |
| 2011/0244562 | A1 | 10/2011 | Davidson et al. |

FOREIGN PATENT DOCUMENTS

| | | | |
|---|---|---|---|
| WO | WO 2004/035765 | A2 | 4/2004 |
| WO | WO 2006/031267 | A2 | 3/2006 |

OTHER PUBLICATIONS

Scherer et al. (Nat. Biotechnol., 2003, 21(12), pp. 1457-1465).*
Zhang et al. (Current Pharmaceutical Biotechnology 2004, vol. 5, p. 1-7).*
European Examination Report for European App. No. 07868926.2, 4 pages, dated Jul. 6, 2011.
European Extended Search Report for European App. No. 07868926.2, 9 pages, dated Nov. 8, 2010.
Bennasser et al., "Competition for XPO5 binding between Dicer mRNA, pre-miRNA and viral RNA regulates human Dicer levels", *Nature Structural & Molecular Biology*, vol. 18, No. 3, pp. 323-327, including one supplemental page, 2011.
Bohnsack et al. "Exportin 5 is a RanGTP-dependent dsRNA-binding protein that mediates nuclear export of pre-miRNAs", *RNA Journal*, vol. 10, pp. 185-191, 2004.
Grimm et al., "Fatality in mice due to oversaturation of cellular microRNA/short hairpin RNA pathways", *Nature*, vol. 441, pp. 537-541, 2006.
Gwizdek et al., "Exportin-5 mediates nuclear export of minihelix-containing RNAs", *The Journal of Biological Chemistry*, vol. 278, No. 8, pp. 5505-5508, 2003.
Gwizdek et al., "Terminal minihelix, a novel RNA motif that directs polymerase III transcripts to the cell cytoplasm: Terminal minihelix and RNA export", *The Journal of Biological Chemistry* vol. 276, No. 28, pp. 25910-25918, 2001.
Kang et al., "Analysis of the RNA Binding Specificity of the Human Tap Protein, a Constitutive Transport Element—Specific Nuclear RNA Export Factor", *Virology*, vol. 262, pp. 200-209, 1999.
Kim, MicroRNA precursors in motion : exportin-5 mediates their nuclear export, *Trends In Cell Biology*, vol. 14, No. 4, pp. 156-159, 2004.
Lindtner, et al. "An element in the 3' untranslated region of human LINE-1 retrotransposon mRNA binds NXF1 (TAP) and can function as a nuclear export element", *RNA Journal*, vol. 8, pp. 345-356, 2002.
Lund et al., "Nuclear Export of MicroRNA Precursors", *Science*, vol. 303, pp. 95-98, 2004.
McManus et al., "Gene silencing using micro-RNA designed hairpins", *RNA*, vol. 8, pp. 842-850, 2002.
McManus et al., "Gene silencing in mammals by small interfering RNAs", *Nature Reviews Genetics*, vol. 3, pp. 737-747, 2002.
Turner et al., "The potential exploitation of plant viral translational enhancers in biotechnology for increased gene expression", *Molecular Biotechnology*, vol. 3, pp. 225-236, 1995.
Yi et al., "Exportin-5 mediates the nuclear export of pre-microRNAs and short hairpin RNAs", *Genes & Development*, 17, 3011-3016 (2003).
Yi et al., "Overexpression of Exportin 5 enhances RNA interference mediated by short hairpin RNAs and microRNAs", *RNA Journal*, vol. 11, pp. 220-226, 2005.
Zeng et al., "Structural requirements for Pre-MicroRNA Binding and Nuclear Export by Exportin 5", *Nucleic Acids Research*, vol. 32, No. 16, pp. 4776-4785, 2004.

* cited by examiner

*Primary Examiner* — Amy Bowman
(74) *Attorney, Agent, or Firm* — Viksnins Harris & Padys PLLP

(57) ABSTRACT

The present invention is directed to nucleic acid molecules containing a loop sequence designed to circumvent exportin-5 mediated export, and methods using these novel molecules.

24 Claims, 8 Drawing Sheets

ALTERNATIVE EXPORT PATHWAYS FOR VECTOR EXPRESSED RNA INTERFERENCE

RELATED APPLICATIONS

This application is a divisional of U.S. patent application Ser. No. 12/515,717, which is a National Stage application under 35 U.S.C. §371 and claims the benefit of priority of International Application No. PCT/US2007/085789, having an International Filing Date of Nov. 28, 2007, which is related to and claims priority under 35 U.S.C. §119(e) to U.S. Provisional Application No. 60/861,500 filed on Nov. 29, 2006, and to U.S. Provisional Application No. 60/861,819 filed on Nov. 30, 2006, which are incorporated by reference herein.

STATEMENT REGARDING FEDERALLY SPONSORED RESEARCH OR DEVELOPMENT

This invention was made with government support under Grant No. NS050210 awarded by the National Institutes of Health. The Government has certain rights in the invention.

BACKGROUND OF THE INVENTION

RNA interference (RNAi) refers to post-transcriptional gene silencing mediated by small double stranded RNAs. Hundreds of non-coding RNAs, called microRNAs, are transcribed from numerous genomes ranging from worms to humans. MicroRNAs are highly conserved and regulate the expression of genes by binding to the 3'-untranslated regions (3'-UTR) of specific mRNAs. Several cellular processing steps produce biologically active, 19-25 nucleotide RNA fragments that, together with a group of proteins called the RNA Induced Silencing Complex (RISC), mediate gene silencing in a sequence-specific fashion. Importantly, endogenous microRNA machinery can be appropriated; vector delivered short hairpin RNAs (shRNAs) can enter the RNAi pathway and induce silencing of any gene of interest.

SUMMARY OF THE INVENTION

The present invention provides for a novel method for exporting vector-expressed RNAi molecules. Currently, shRNA and miRNAs that are expressed from viral or plasmid vectors use the export pathway mediated in part by Exprotin-V. It is now known that this pathway can be saturated, leading to deleterious effects on the cells' native microRNA processing pathway. The present invention uses the nxf-export pathway for RNAi. This pathway is more amenable to RNAi because it is less saturable, and therefore is more favorable to the cell.

The present invention provides an isolated nucleic acid molecule containing a first portion, wherein the first portion is no more than 30 nucleotides in length; a second portion, wherein the second portion has a sequence that is complementary to the first portion; and a loop portion comprising a sequence designed to circumvent exportin-5 mediated export; wherein the first portion and the second portion are operably linked by means of the loop portion to form a hairpin structure comprising a duplex structure and a loop structure.

In certain embodiments, the loop portion is about 12 to 50 nucleotides long, or is about 20 to 40 nucleotides long, or is about 25 to 35 nucleotides long, or is about 30 nucleotides long. In certain embodiments, the loop portion is a 32 nucleotide L1 motif. In certain embodiments, the loop portion comprises between 12 and 32 nucleotides of SEQ ID NO:1. In certain embodiments, the loop portion comprises between 12 and 32 contiguous nucleotides of SEQ ID NO:1. In certain embodiments, the loop portion consists of SEQ ID NO:4, SEQ ID NO:5, or SEQ ID NO:6.

In certain embodiments, the duplex is less than 30 nucleotides in length, such as from 19 to 25 nucleotides in length.

In certain embodiments, the nucleic acid molecule further comprises an overhang region, such as a 3' overhang region, a 5' overhang region, or both a 3' and a 5' overhang region. In certain embodiments, the overhang region is from 1 to 10 nucleotides in length.

In certain embodiments, the nucleic acid molecule is a short hairpin RNA (shRNA). In certain embodiments, the nucleic acid molecule is a microRNA (miRNA).

The present invention also provides an expression cassette comprising a sequence encoding a nucleic acid molecule containing a first portion, wherein the first portion is no more than 30 nucleotides in length; a second portion, wherein the second portion has a sequence that is complementary to the first portion; and a loop portion comprising a sequence designed to circumvent exportin-5 mediated export; wherein the first portion and the second portion are operably linked by means of the loop portion to form a hairpin structure comprising a duplex structure and a loop structure. In certain embodiments, the expression cassette further contains a promoter. In certain embodiments, the promoter is a regulatable promoter. In certain embodiments, the promoter is a constitutive promoter. In certain embodiments, the promoter is a CMV, RSV, or polIII promoter. In certain embodiments, the promoter is not a polIII promoter.

The present invention provides a vector containing the expression cassette described above. In certain embodiments, the vector is a viral vector. In certain embodiments, the viral vector is an adenoviral, lentiviral, adeno-associated viral (AAV), poliovirus, HSV, or murine Maloney-based viral vector.

The present invention also provides methods of reducing the expression of a gene product in a cell by contacting a cell with a nucleic acid molecule containing a first portion, wherein the first portion is no more than 30 nucleotides in length; a second portion, wherein the second portion has a sequence that is complementary to the first portion; and a loop portion comprising a sequence designed to circumvent exportin-5 mediated export; wherein the first portion and the second portion are operably linked by means of the loop portion to form a hairpin structure comprising a duplex structure and a loop structure.

The present invention provides a method of suppressing the accumulation of a target protein in a cell by introducing a nucleic acid molecule described above into the cell in an amount sufficient to suppress accumulation of the target protein in the cell. In certain embodiments, the accumulation of target protein is suppressed by at least 10%. The accumulation of target protein is suppressed by at least 10%, 20%, 30%, 40%, 50%, 60%, 70%, 80%, 90% 95%, or 99%.

The present invention provides a method to inhibit expression of a target protein gene in a cell by introducing a nucleic acid molecule described above into the cell in an amount sufficient to inhibit expression of the target protein, and wherein the RNA inhibits expression of the target protein gene. The target protein is inhibited by at least 10%, 20%, 30%, 40%, 50%, 60%, 70%, 80%, 90% 95%, or 99%.

As used herein, the term "overhang region" means a portion of the RNA that does not bind with the second strand. Further, the first strand and the second strand encoding the duplex can be operably linked by means of an RNA loop strand to form a hairpin structure comprising a duplex structure and a loop structure. Such RNAi molecules with hairpin stem-loop structure are referred to sometimes as short hairpin RNAs or shRNAs.

The reference to "siRNAs" herein is meant to include shRNAs, microRNAs and other small RNAs that can or are capable of modulating the expression of a target gene via RNA interference. Such small RNAs include without limitation, shRNAs and miroRNAs (miRNAs).

These cassettes and vectors may be contained in a cell, such as a mammalian cell. A non-human mammal may contain the cassette or vector.

"Neurological disease" and "neurological disorder" refer to both hereditary and sporadic conditions that are characterized by nervous system dysfunction, and which may be associated with atrophy of the affected central or peripheral nervous system structures, or loss of function without atrophy. A neurological disease or disorder that results in atrophy is commonly called a "neurodegenerative disease" or "neurodegenerative disorder." Neurodegenerative diseases and disorders include, but are not limited to, amyotrophic lateral sclerosis (ALS), hereditary spastic hemiplegia, primary lateral sclerosis, spinal muscular atrophy, Kennedy's disease, Alzheimer's disease, Parkinson's disease, multiple sclerosis, and repeat expansion neurodegenerative diseases, e.g., diseases associated with expansions of trinucleotide repeats such as polyglutamine (polyQ) repeat diseases, e.g., Huntington's disease (HD), spinocerebellar ataxia (SCA1, SCA2, SCA3, SCA6, SCA7, and SCA17), spinal and bulbar muscular atrophy (SBMA), dentatorubropallidoluysian atrophy (DRPLA). An example of a disabling neurological disorder that does not appear to result in atrophy is DYT1 dystonia. The gene of interest may encode a ligand for a chemokine involved in the migration of a cancer cell, or a chemokine receptor.

The present invention further provides a method of substantially silencing a target gene of interest or targeted allele for the gene of interest in order to provide a therapeutic effect. As used herein the term "substantially silencing" or "substantially silenced" refers to decreasing, reducing, or inhibiting the expression of the target gene or target allele by at least about 5%, 10%, 15%, 20%, 25%, 30%, 35%, 40%, 45%, 50%, 55%, 60%, 65%, 70%, 75%, 80%, 85% to 100%. As used herein the term "therapeutic effect" refers to a change in the associated abnormalities of the disease state, including pathological and behavioral deficits; a change in the time to progression of the disease state; a reduction, lessening, or alteration of a symptom of the disease; or an improvement in the quality of life of the person afflicted with the disease. Therapeutic effect can be measured quantitatively by a physician or qualitatively by a patient afflicted with the disease state targeted by the RNAi molecule. In certain embodiments wherein both the mutant and wild type allele are substantially silenced, the term therapeutic effect defines a condition in which silencing of the wild type allele's expression does not have a deleterious or harmful effect on normal functions such that the patient would not have a therapeutic effect.

In one embodiment, the selected nucleotide sequence is operably linked to control elements that direct the transcription or expression thereof in the subject in vivo. Such control elements can comprise control sequences normally associated with the selected gene. Alternatively, heterologous control sequences can be employed. Useful heterologous control sequences generally include those derived from sequences encoding mammalian or viral genes. Examples include, but are not limited to, the SV40 early promoter, mouse mammary tumor virus LTR promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, pol II promoters, pol III promoters, synthetic promoters, hybrid promoters, and the like. In addition, sequences derived from nonviral genes, such as the murine metallothionein gene, will also find use herein. Such promoter sequences are commercially available from, e.g., Stratagene (San Diego, Calif.).

In one embodiment, both heterologous promoters and other control elements, such as CNS-specific and inducible promoters, enhancers and the like, will be of particular use. Examples of heterologous promoters include the CMB promoter. Examples of CNS-specific promoters include those isolated from the genes from myelin basic protein (MBP), glial fibrillary acid protein (GFAP), and neuron specific enolase (NSE). Examples of inducible promoters include DNA responsive elements for ecdysone, tetracycline, hypoxia and aufin.

Methods of delivery of viral vectors include, but are not limited to, intra-arterial, intra-muscular, intravenous, intranasal and oral routes. Generally, rAAV virions may be introduced into cells of the CNS using either in vivo or in vitro transduction techniques. If transduced in vitro, the desired recipient cell will be removed from the subject, transduced with rAAV virions and reintroduced into the subject. Alternatively, syngeneic or xenogeneic cells can be used where those cells will not generate an inappropriate immune response in the subject.

Suitable methods for the delivery and introduction of transduced cells into a subject have been described. For example, cells can be transduced in vitro by combining recombinant AAV virions with CNS cells e.g., in appropriate media, and screening for those cells harboring the DNA of interest can be screened using conventional techniques such as Southern blots and/or PCR, or by using selectable markers. Transduced cells can then be formulated into pharmaceutical compositions, described more fully below, and the composition introduced into the subject by various techniques, such as by grafting, intramuscular, intravenous, subcutaneous and intraperitoneal injection.

Any convection-enhanced delivery device may be appropriate for delivery of viral vectors. In one embodiment, the device is an osmotic pump or an infusion pump. Both osmotic and infusion pumps are commercially available from a variety of suppliers, for example Alzet Corporation, Hamilton Corporation, Aiza, Inc., Palo Alto, Calif.). Typically, a viral vector is delivered via CED devices as follows. A catheter, cannula or other injection device is inserted into CNS tissue in the chosen subject. In view of the teachings herein, one of skill in the art could readily determine which general area of the CNS is an appropriate target. For example, when delivering AAV vector encoding a therapeutic gene to treat PD, the striatum is a suitable area of the brain to target. Stereotactic maps and positioning devices are available, for example from ASI Instruments, Warren, Mich. Positioning may also be conducted by using anatomical maps obtained by CT and/or MRI imaging of the subject's brain to help guide the injection device to the chosen target. Moreover, because the methods described herein can be practiced such that relatively large areas of the brain take up the viral vectors, fewer infusion cannula are needed. Since surgical complications are related to the number of penetrations, the methods described herein also serve to reduce the side effects seen with conventional delivery techniques.

In one embodiment, pharmaceutical compositions will comprise sufficient genetic material to produce a therapeutically effective amount of the RNAi molecule of interest, i.e., an amount sufficient to reduce or ameliorate symptoms of the disease state in question or an amount sufficient to confer the desired benefit. The pharmaceutical compositions will also contain a pharmaceutically acceptable excipient. Such excipients include any pharmaceutical agent that does not itself induce the production of antibodies harmful to the individual receiving the composition, and which may be administered without undue toxicity.

Pharmaceutically acceptable excipients include, but are not limited to, sorbitol, Tween80, and liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in Remington's Pharmaceutical Sciences (Mack Pub. Co., N.J. 1991).

As is apparent to those skilled in the art in view of the teachings of this specification, an effective amount of viral vector which must be added can be empirically determined Administration can be effected in one dose, continuously or intermittently throughout the course of treatment. Methods of determining the most effective means and dosages of administration are well known to those of skill in the art and will vary with the viral vector, the composition of the therapy, the target cells, and the subject being treated. Single and multiple administrations can be carried out with the dose level and pattern being selected by the treating physician.

BRIEF DESCRIPTION OF THE FIGURES

This patent or application file contains at least one drawing executed in color. Copies of this patent or patent application publication with color drawing(s) will be provided by the Office upon request and payment of the necessary fee.

DETAILED DESCRIPTION OF THE INVENTION

Modulation of gene expression by endogenous, noncoding RNAs is increasingly appreciated as a mechanism playing a role in eukaryotic development, maintenance of chromatin structure and genomic integrity (McManus, 2002). Techniques have been developed to trigger RNA interference (RNAi) against specific targets in mammalian cells by introducing exogenously produced or intracellularly expressed siRNAs. These methods have proven to be quick, inexpensive and effective for knockdown experiments in vitro and in vivo. The ability to accomplish selective gene silencing has led to the hypothesis that siRNAs might be employed to suppress gene expression for therapeutic benefit.

Figure 1:
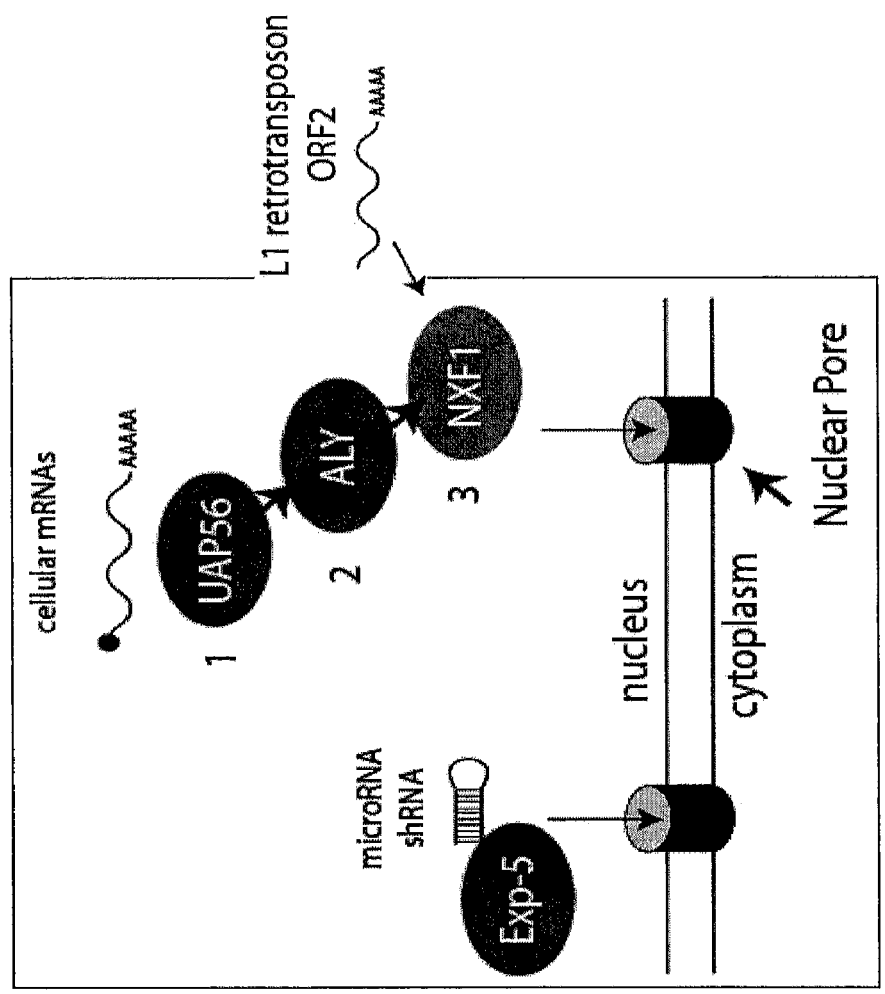
FIG. 1: Exportin-5 Mediated Export of microRNA and shRNA. Cartoon of the two export pathways described in this application. One, the Exportin-5 pathway is commonly used in shRNA and miRNA expression vector systems.
Figure 2:
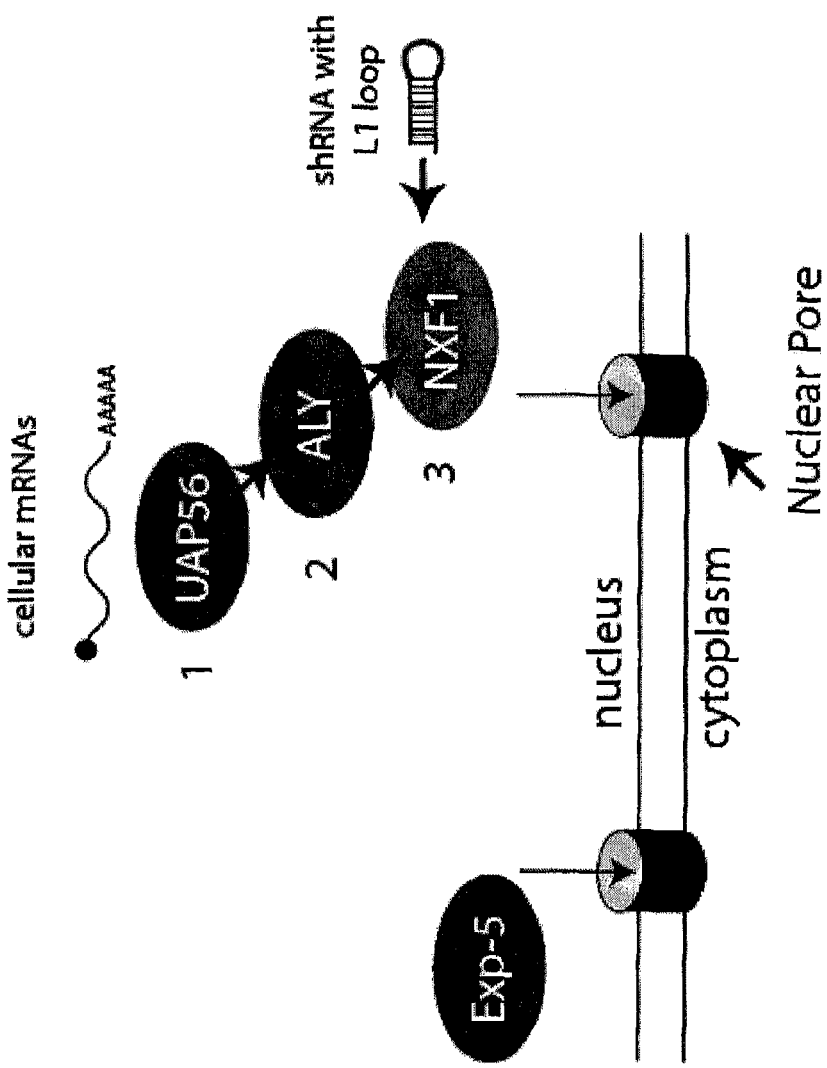
FIG. 2: Redirecting shRNA Nuclear Export. Most small RNAs are exported through the exportin-5 mediated pathway. The UAP56/ALY/NXF1 pathway can be utilized by placing NXF1 recognition sequences into the loop region of a hairpin (either miRNA or shRNA), which when processed, releases an siRNA.

The potential for RNAi as a therapeutic tool for treating dominant genetics disorders, chronic viral infections, and cancer is immense. However, recent work by Grimm, et al. (*Nature*, 441(7092):537-41 (2006)) and the inventors' own data suggest that the microRNA processing pathway can be saturated by over-expression of shRNAs, leading to cellular toxicity. Current data suggest that saturation of the nuclear export factor exportin-5 is the primary cause of shRNA-induced toxicity. The inventors incorporated specific sequences designed to circumvent exportin-5 mediated export into the shRNA loop to relieve this toxicity. To do this, the inventors used a repeated sequence motif derived from the ORF2 transcript of an L1 retrotransposon that mediates Nxf-1 mediated nuclear export of viral mRNAs (FIGS. 1 and 2).

Figure 3B:
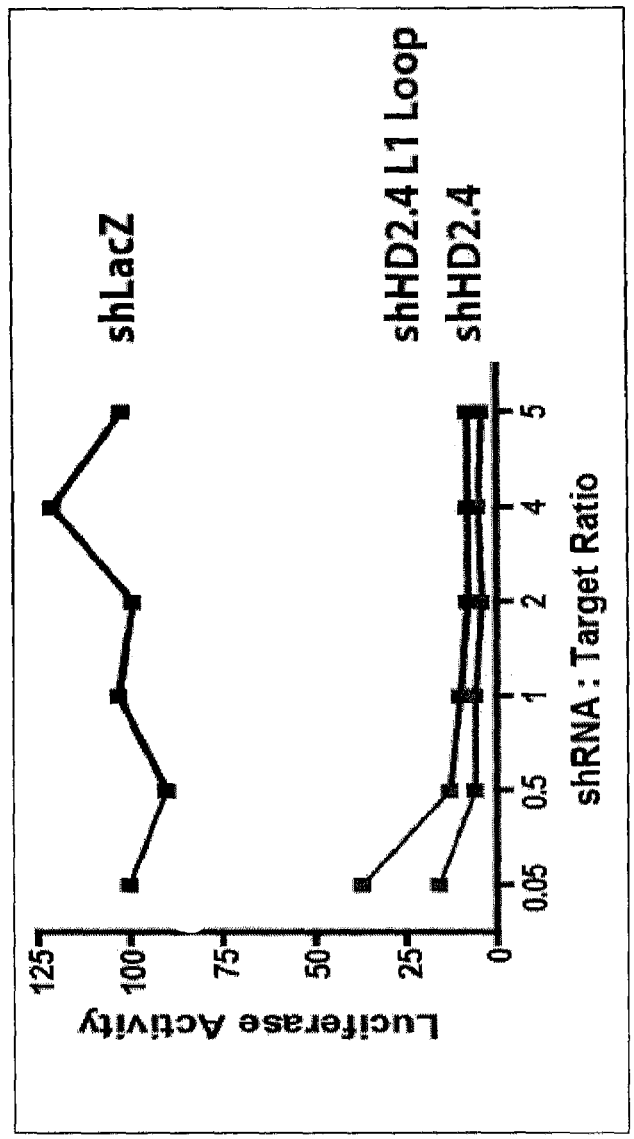
FIGS. 3A and 3B: shRNAs with L1 Loop Are Functional.
Figure 3A:
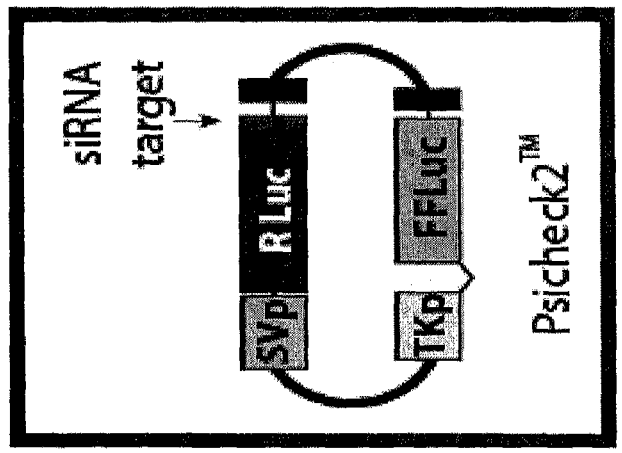

The inventors found that shRNAs and microRNAs in which the standard 10 nucleotide (nt) loop sequence was replaced by the 32 nt L1 motif (L1 loop) were functional and elicited equivalent levels of gene silencing of artificial luciferase targets (FIGS. 3A and 3B). A reporter vector was generated containing the siRNA target in the 3' UTR of *Renilla* luciferase. For this experiment, the siRNA target allowed silencing by shHD2.4, but not shlacZ. As shown in FIG. 3B, the standard shHD2.4, which is exported via exportin-5 from the nucleus, silences the R-luc activity by greater than 90%, even at very low shRNA to target ratios. Unexpectedly, placing the L1 sequences into the loop (shHD2.4L1) for redirecting export to the UAP56/ALY/NXF1pathway allowed for export and processing. Silencing was nearly as efficient as for shHD2.4.

Figure 4:
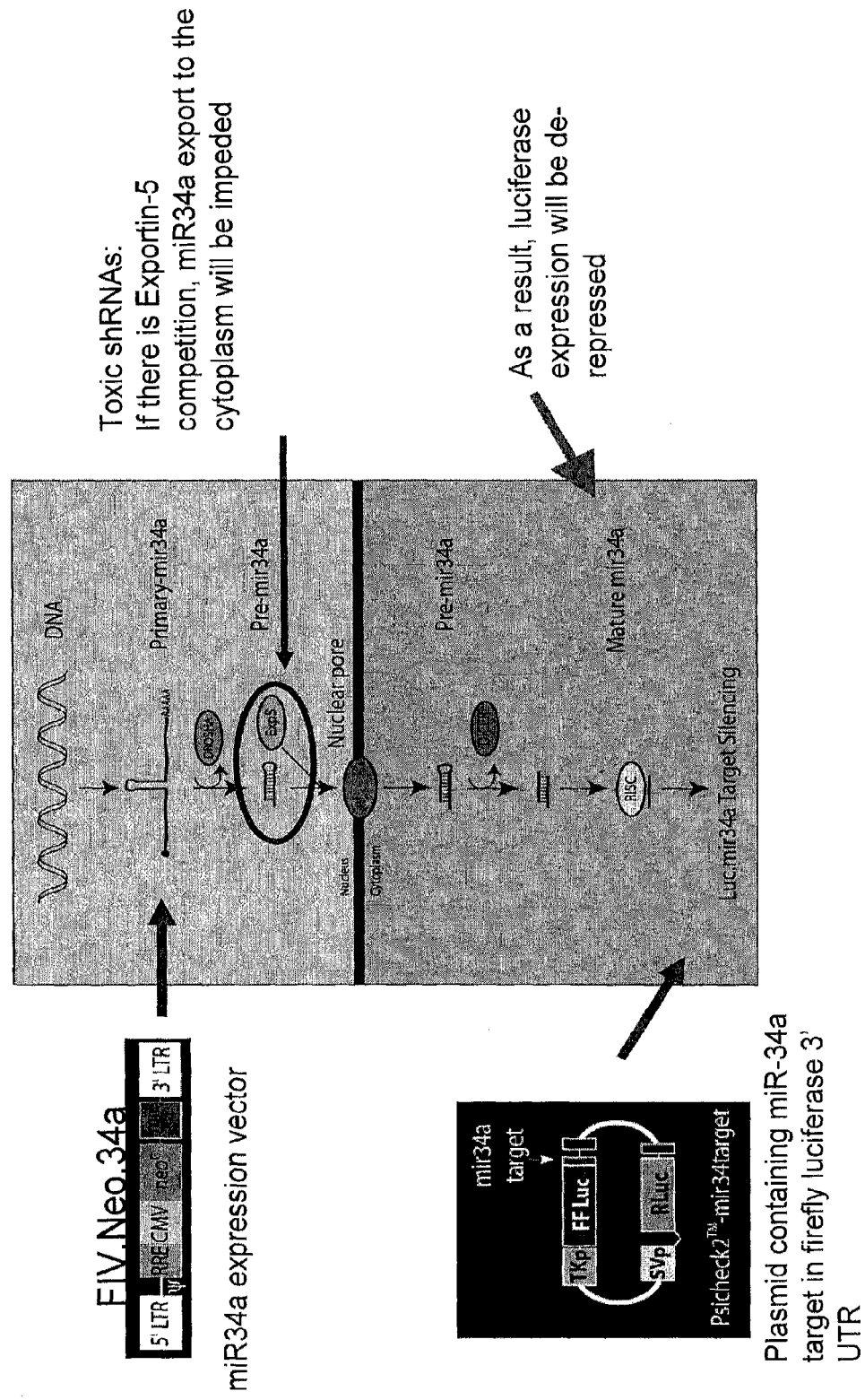
FIG. 4 depicts an shRNA competition assay.
Figure 5:
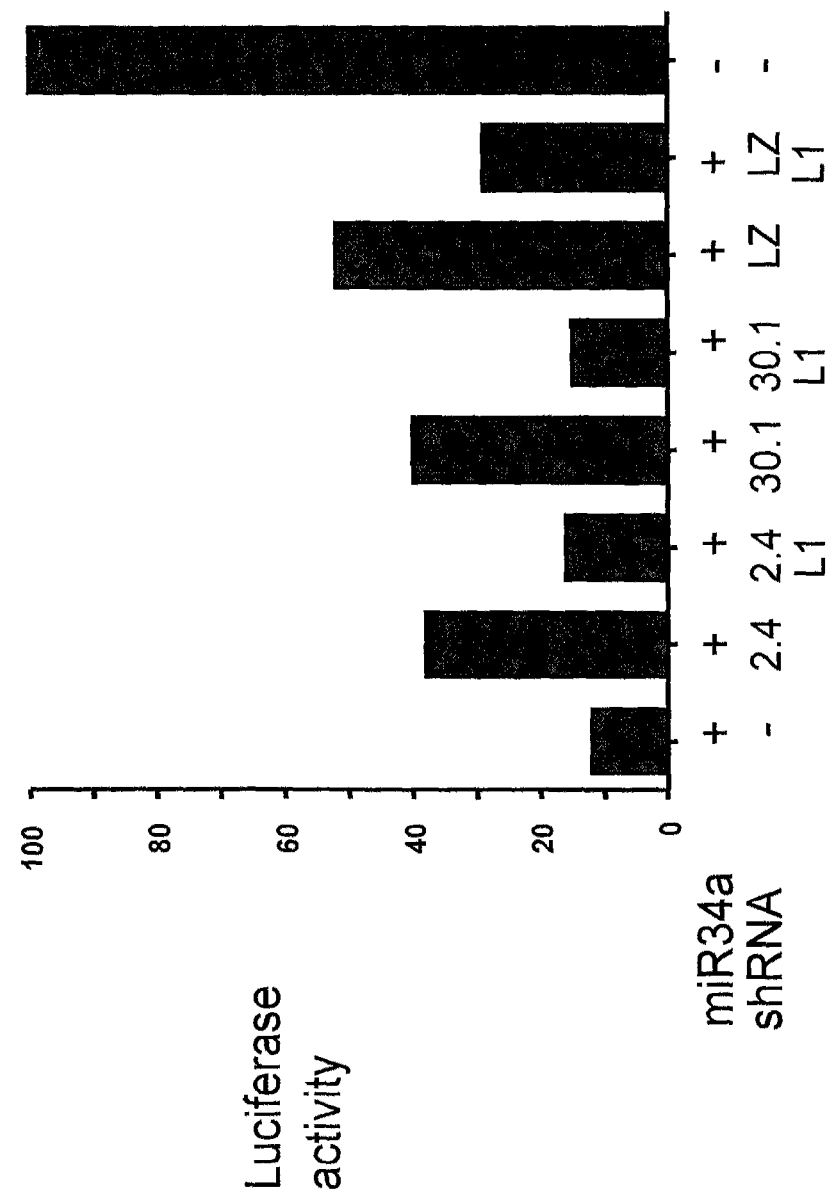
FIG. 5: Reducing potential shRNA toxicity with retargeted nuclear export.

The inventors examined if there was reduced toxicity with retargeted nuclear export (FIGS. 4 and 5). As outlined in the cartoon in FIG. 4, cells were transfected with plasmids expressing miR34a and the shRNAs encoding HD2.4, HD30.a or shLacZ (LZ) as indicated above, and luciferase activity measured. With no miR-34a activity (FIG. 5, far right) luciferase is set to 100%. Plasmids expressing luciferase with a miR34a target sequence in the 3' UTR was silenced approximately 90% by miR34a in the absence of exogenous shRNA expression vectors. While the shRNA expression plasmids 2.4, 30.1 and LZ inhibited miR34a export, inclusion of the L1 loop alleviated this depression. The data in FIGS. 3 and 5 show that the shRNAs with L1 sequences in the loop can support silencing, and that these sequences are likely not exported through exportin 5 and therefore do not inhibit processing of miRNAs.

Disclosed herein is a strategy that results in substantial silencing of targeted alleles via RNAi. However, this strategy was not known to be successful, since inhibitory RNAs have not been shown to use this export pathway. Indeed, it was not known what level of silencing to expect from shRNAs containing L1 sequences in their loops. Impressively, the inventors found that the L1 sequence was tolerated, and silencing was as efficacious as a standard miRNA loop. Also importantly, the L1 loop did not suppress miRNA processing.

Use of this strategy results in markedly diminished expression of targeted alleles. This strategy is useful in reducing expression of targeted alleles in order to model biological processes or to provide therapy for human diseases. For example, this strategy can be applied to a major class of neurodegenerative disorders, the polyglutamine diseases, as is demonstrated by the reduction of polyglutamine aggregation in cells following application of the strategy. As used herein the term "substantial silencing" means that the mRNA of the targeted allele is inhibited and/or degraded by the presence of the introduced RNAi molecule, such that expression of the targeted allele is reduced by about 10% to 100% as compared to the level of expression seen when the RNAi molecule is not present. Generally, when an allele is substantially silenced, it will have at least 40%, 50%, 60%, to 70%, e.g., 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, 98%, 99% or even 100% reduction expression as compared to when the RNAi molecule is not present. As used herein the term "substantially normal activity" means the level of expression of an allele when an RNAi molecule has not been introduced to a cell.

One of skill in the art can select target sites for generating specific RNAi molecules. Such RNAi molecules may be designed using the guidelines provided by Ambion (Austin, Tex.). Briefly, the target cDNA sequence is scanned for target sequences that had AA di-nucleotides. Sense and anti-sense oligonucleotides are generated to these targets (AA+3' adjacent 19 nucleotides) that contained a G/C content of 35 to 55%. These sequences are then compared to others in the human genome database to minimize homology to other known coding sequences (BLAST search).

To accomplish intracellular expression of the therapeutic RNAi, an RNAi molecule is constructed containing a hairpin sequence (such as a 21-bp duplex) representing sequences directed against the gene of interest. The RNAi molecule, or a nucleic acid encoding the RNAi molecule, is introduced to the target cell, such as a diseased brain cell. The RNAi molecule reduces target mRNA and protein expression.

The construct encoding the therapeutic RNAi molecule can be configured such that one or more strands of the RNAi molecule are encoded by a nucleic acid that is immediately contiguous to a promoter. In one example, the promoter is a pol II promoter. If a pol II promoter is used in a particular construct, it is selected from readily available pol II promoters known in the art, depending on whether regulatable, inducible, tissue or cell-specific expression of the RNAi molecule is desired. The construct is introduced into the target cell, such as by injection, allowing for diminished target-gene expression in the cell.

The present invention provides an expression cassette containing an isolated nucleic acid sequence encoding a RNAi molecule targeted against a gene of interest. The RNAi molecule forms a hairpin structure that contains a duplex structure and a loop structure. The duplex is less than 30 nucleotides in length, such as from 19 to 25 nucleotides. The RNAi molecule may further contain an overhang region. Such an overhang may be a 3' overhang region or a 5' overhang region. The overhang region may be, for example, from 1 to 6 nucleotides in length. The expression cassette may further contain a pol II promoter, as described herein. Examples of pol II promoters include regulatable promoters and constitutive promoters. For example, the promoter may be a CMV or RSV promoter. The expression cassette may further contain a polyadenylation signal, such as a synthetic minimal polyadenylation signal. The nucleic acid sequence may further contain a marker gene or stuffer sequences. The expression cassette may be contained in a viral vector. An appropriate viral vector for use in the present invention may be an adenoviral, lentiviral, adeno-associated viral (AAV), poliovirus, herpes simplex virus (HSV) or murine Maloney-based viral vector. The gene of interest may be a gene associated with a condition amenable to RNAi therapy. Examples of such conditions include neurodegenerative diseases, such as a trinucleotide-repeat disease (e.g., polyglutamine repeat disease). Examples of these diseases include Huntington's disease or several spinocerebellar ataxias. Alternatively, the gene of interest may encode a ligand for a chemokine involved in the migration of a cancer cell, or a chemokine receptor.

The present invention also provides an expression cassette containing an isolated nucleic acid sequence encoding a first segment, a second segment located immediately 3' of the first segment, and a third segment located immediately 3' of the second segment, wherein the first and third segments are each less than 30 base pairs in length and each more than 10 base pairs in length, and wherein the sequence of the third segment is the complement of the sequence of the first segment, and wherein the isolated nucleic acid sequence functions as a RNAi molecule targeted against a gene of interest. The expression cassette may be contained in a vector, such as a viral vector or a plasmid vector.

The present invention provides a method of reducing the expression of a gene product in a cell by contacting a cell with an expression cassette described above. It also provides a method of treating a patient by administering to the patient a composition of the expression cassette described above.

The present invention further provides a method of reducing the expression of a gene product in a cell by contacting a cell with an expression cassette containing an isolated nucleic acid sequence encoding a first segment, a second segment located immediately 3' of the first segment, and a third segment located immediately 3' of the second segment, wherein the first and third segments are each less than 30 base pairs in length and each more than 10 base pairs in length, and wherein the sequence of the third segment is the complement of the sequence of the first segment, and wherein the isolated nucleic acid sequence functions as a RNAi molecule targeted against a gene of interest.

The present method also provides a method of treating a patient, by administering to the patient a composition containing an expression cassette, wherein the expression cassette contains an isolated nucleic acid sequence encoding a first segment, a second segment located immediately 3' of the first segment, and a third segment located immediately 3' of the second segment, wherein the first and third segments are each less than 30 bases in length and each more than 10 bases in length, and wherein the sequence of the third segment is the complement of the sequence of the first segment, and wherein the isolated nucleic acid sequence functions as a RNAi molecule targeted against a gene of interest.

I. RNA Interference Molecules

A "small interfering RNA" or "short interfering RNA" or "siRNA" or "short hairpin RNA" or "shRNA" or "microRNA" or "an RNAi molecule" is a RNA duplex of nucleotides that is targeted to a nucleic acid sequence of interest, for example, a Huntington's Disease gene (also referred to as huntingtin, htt, or HD). As used herein, the term "siRNA" is a generic term that encompasses the subset of shRNAs. A "RNA duplex" refers to the structure formed by the complementary pairing between two regions of a RNA molecule. An RNAi molecule is "targeted" to a gene in that the nucleotide sequence of the duplex portion of the RNAi molecule is complementary to a nucleotide sequence of the targeted gene. In certain embodiments, the siRNAs are targeted to the sequence encoding huntingtin. In some embodiments, the length of the duplex of siRNAs is less than 30 base pairs. In some embodiments, the duplex can be 29, 28, 27, 26, 25, 24, 23, 22, 21, 20, 19, 18, 17, 16, 15, 14, 13, 12, 11 or 10 base pairs in length. In some embodiments, the length of the duplex is 19 to 25 base pairs in length. In certain embodiment, the length of the duplex is 19 or 21 base pairs in length. The RNA duplex portion of the RNAi molecule can be part of a hairpin structure.

In addition to the duplex portion, the hairpin structure contains a loop portion positioned between the two sequences that form the duplex. The loop can vary in length. In some embodiments the loop is 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length. In certain embodiments, the loop portion is a 30 nucleotide L1 motif. The loop portion contains a sequence designed to circumvent exportin-5 mediated export.

The hairpin structure can also contain 3' or 5' overhang portions. In some embodiments, the overhang is a 3' or a 5' overhang 0, 1, 2, 3, 4 or 5 nucleotides in length.

The RNAi molecule can be encoded by a nucleic acid sequence, and the nucleic acid sequence can also include a promoter. The nucleic acid sequence can also include a polyadenylation signal. In some embodiments, the polyadenylation signal is a synthetic minimal polyadenylation signal.

"Knock-down," "knock-down technology" refers to a technique of gene silencing in which the expression of a target gene is reduced as compared to the gene expression prior to the introduction of the RNAi molecule, which can lead to the inhibition of production of the target gene product. The term "reduced" is used herein to indicate that the target gene expression is lowered by 1-100%. In other words, the amount of RNA available for translation into a polypeptide or protein is minimized. For example, the amount of protein may be reduced by 10, 20, 30, 40, 50, 60, 70, 80, 90, 95, or 99%. In some embodiments, the expression is reduced by about 90% (i.e., only about 10% of the amount of protein is observed a cell as compared to a cell where RNAi molecules have not been administered). Knock-down of gene expression can be directed by the use of dsRNAs or siRNAs.

"RNA interference (RNAi)" is the process of sequence-specific, post-transcriptional gene silencing initiated by RNAi molecules. During RNAi, RNAi molecules induce degradation of target mRNA with consequent sequence-specific inhibition of gene expression.

According to a method of the present invention, the expression of huntingtin can be modified via RNAi. For example, the accumulation of huntingtin can be suppressed in a cell. The term "suppressing" refers to the diminution, reduction or elimination in the number or amount of transcripts present in a particular cell. For example, the accumulation of mRNA encoding huntingtin can be suppressed in a cell by RNA interference (RNAi), e.g., the gene is silenced by sequence-specific double-stranded RNA (dsRNA), which is also called short interfering RNA (siRNA). These siRNAs can be two separate RNA molecules that have hybridized together, or they may be a single hairpin wherein two portions of a RNA molecule have hybridized together to form a duplex.

A mutant protein refers to the protein encoded by a gene having a mutation, e.g., a missense or nonsense mutation in one or both alleles of huntingtin. A mutant huntingtin may be disease-causing, i.e., may lead to a disease associated with the presence of huntingtin in an animal having either one or two mutant allele(s). The term "nucleic acid" refers to deoxyribonucleotides or ribonucleotides and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues.

A "nucleic acid fragment" is a portion of a given nucleic acid molecule. Deoxyribonucleic acid (DNA) in the majority of organisms is the genetic material while ribonucleic acid (RNA) is involved in the transfer of information contained within DNA into proteins.

The term "nucleotide sequence" refers to a polymer of DNA or RNA which can be single- or double-stranded, optionally containing synthetic, non-natural or altered nucleotide bases capable of incorporation into DNA or RNA polymers.

The terms "nucleic acid," "nucleic acid molecule," "nucleic acid fragment," "nucleic acid sequence or segment," or "polynucleotide" are used interchangeably and may also be used interchangeably with gene, cDNA, DNA and RNA encoded by a gene.

The invention encompasses isolated or substantially purified nucleic acid or protein compositions. In the context of the present invention, an "isolated" or "purified" DNA molecule or RNA molecule or an "isolated" or "purified" polypeptide is a DNA molecule, RNA molecule, or polypeptide that exists apart from its native environment and is therefore not a product of nature. An isolated DNA molecule, RNA molecule or polypeptide may exist in a purified form or may exist in a non-native environment such as, for example, a transgenic host cell. For example, an "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein or polypeptide having less than about 30%, 20%, 10%, or 5% (by dry weight) of contaminating protein. When the protein of the invention, or biologically active portion thereof, is recombinantly produced, culture medium represents less than about 30%, 20%, 10%, or 5% (by dry weight) of chemical precursors or non-protein-of-interest chemicals. Fragments and variants of the disclosed nucleotide sequences and proteins or partial-length proteins encoded thereby are also encompassed by the present invention. By "fragment" or "portion" is meant a full length or less than full length of the nucleotide sequence encoding, or the amino acid sequence of, a polypeptide or protein.

The term "gene" is used broadly to refer to any segment of nucleic acid associated with a biological function. Thus, genes include coding sequences and/or the regulatory sequences required for their expression. For example, "gene" refers to a nucleic acid fragment that expresses mRNA, functional RNA, or specific protein, including regulatory sequences. "Genes" also include nonexpressed DNA segments that, for example, form recognition sequences for other proteins. "Genes" can be obtained from a variety of sources, including cloning from a source of interest or synthesizing from known or predicted sequence information, and may include sequences designed to have desired parameters. An "allele" is one of several alternative forms of a gene occupying a given locus on a chromosome.

"Naturally occurring," "native" or "wildtype" are used to describe an object that can be found in nature as distinct from being artificially produced. For example, a protein or nucleotide sequence present in an organism (including a virus), which can be isolated from a source in nature and which has not been intentionally modified by a person in the laboratory, is naturally occurring.

The term "chimeric" refers to a gene or DNA that contains 1) DNA sequences, including regulatory and coding sequences that are not found together in nature or 2) sequences encoding parts of proteins not naturally adjoined, or 3) parts of promoters that are not naturally adjoined. Accordingly, a chimeric gene may include regulatory sequences and coding sequences that are derived from different sources, or include regulatory sequences and coding sequences derived from the same source, but arranged in a manner different from that found in nature.

A "transgene" refers to a gene that has been introduced into the genome by transformation. Transgenes include, for example, DNA that is either heterologous or homologous to the DNA of a particular cell to be transformed. Additionally, transgenes may include native genes inserted into a non-native organism, or chimeric genes.

The term "endogenous gene" refers to a native gene in its natural location in the genome of an organism.

A "foreign" gene refers to a gene not normally found in the host organism that has been introduced by gene transfer.

The terms "protein," "peptide" and "polypeptide" are used interchangeably herein.

A "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of molecular biology techniques, as, for example, with polymerase chain reaction (PCR) and hybridization techniques. Variant nucleotide sequences also include synthetically derived nucleotide sequences, such as those generated, for example, by using site-directed mutagenesis, which encode the native protein, as well as those that encode a polypeptide having amino acid substitutions. Generally, nucleotide sequence variants of the invention will have at least 40%, 50%, 60%, to 70%, e.g., 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to the native (endogenous) nucleotide sequence.

"Conservatively modified variations" of a particular nucleic acid sequence refers to those nucleic acid sequences that encode identical or essentially identical amino acid sequences. Because of the degeneracy of the genetic code, a large number of functionally identical nucleic acids encode any given polypeptide. For instance, the codons CGT, CGC, CGA, CGG, AGA and AGG all encode the amino acid arginine. Thus, at every position where an arginine is specified by a codon, the codon can be altered to any of the corresponding codons described without altering the encoded protein. Such nucleic acid variations are "silent variations," which are one species of "conservatively modified variations." Every nucleic acid sequence described herein that encodes a polypeptide also describes every possible silent variation, except where otherwise noted. One of skill in the art will recognize that each codon in a nucleic acid (except ATG, which is ordinarily the only codon for methionine) can be modified to yield a functionally identical molecule by standard techniques. Accordingly, each "silent variation" of a nucleic acid that encodes a polypeptide is implicit in each described sequence.

"Recombinant DNA molecule" is a combination of DNA sequences that are joined together using recombinant DNA technology and procedures used to join together DNA sequences as described, for example, in Sambrook and Russell (2001).

The terms "heterologous gene," "heterologous DNA sequence," "exogenous DNA sequence," "heterologous RNA sequence," "exogenous RNA sequence" or "heterologous nucleic acid" each refer to a sequence that either originates from a source foreign to the particular host cell, or is from the same source but is modified from its original or native form. Thus, a heterologous gene in a host cell includes a gene that is endogenous to the particular host cell but has been modified through, for example, the use of DNA shuffling. The terms also include non-naturally occurring multiple copies of a naturally occurring DNA or RNA sequence. Thus, the terms refer to a DNA or RNA segment that is foreign or heterologous to the cell, or homologous to the cell but in a position within the host cell nucleic acid in which the element is not ordinarily found. Exogenous DNA segments are expressed to yield exogenous polypeptides.

A "homologous" DNA or RNA sequence is a sequence that is naturally associated with a host cell into which it is introduced.

"Wild-type" refers to the normal gene or organism found in nature.

"Genome" refers to the complete genetic material of an organism.

A "vector" is defined to include, inter alia, any viral vector, as well as any plasmid, cosmid, phage or binary vector in double or single stranded linear or circular form that may or may not be self transmissible or mobilizable, and that can transform prokaryotic or eukaryotic host either by integration into the cellular genome or exist extrachromosomally (e.g., autonomous replicating plasmid with an origin of replication).

"Expression cassette" as used herein means a nucleic acid sequence capable of directing expression of a particular nucleotide sequence in an appropriate host cell, which may include a promoter operably linked to the nucleotide sequence of interest that may be operably linked to termination signals. It also may include sequences required for proper translation of the nucleotide sequence. The coding region usually codes for a protein of interest but may also code for a functional RNA of interest, for example an antisense RNA, a nontranslated RNA in the sense or antisense direction, or an RNAi molecule. The expression cassette including the nucleotide sequence of interest may be chimeric. The expression cassette may also be one that is naturally occurring but has been obtained in a recombinant form useful for heterologous expression. The expression of the nucleotide sequence in the expression cassette may be under the control of a constitutive promoter or of an regulatable promoter that initiates transcription only when the host cell is exposed to some particular stimulus. In the case of a multicellular organism, the promoter can also be specific to a particular tissue or organ or stage of development.

Such expression cassettes can include a transcriptional initiation region linked to a nucleotide sequence of interest. Such an expression cassette is provided with a plurality of restriction sites for insertion of the gene of interest to be under the transcriptional regulation of the regulatory regions. The expression cassette may additionally contain selectable marker genes.

"Coding sequence" refers to a DNA or RNA sequence that codes for a specific amino acid sequence. It may constitute an "uninterrupted coding sequence", i.e., lacking an intron, such as in a cDNA, or it may include one or more introns bounded by appropriate splice junctions. An "intron" is a sequence of RNA that is contained in the primary transcript but is removed through cleavage and re-ligation of the RNA within the cell to create the mature mRNA that can be translated into a protein.

The term "open reading frame" (ORF) refers to the sequence between translation initiation and termination codons of a coding sequence. The terms "initiation codon" and "termination codon" refer to a unit of three adjacent nucleotides (a 'codon') in a coding sequence that specifies initiation and chain termination, respectively, of protein synthesis (mRNA translation).

"Functional RNA" refers to sense RNA, antisense RNA, ribozyme RNA, siRNA, or other RNA that may not be translated but yet has an effect on at least one cellular process.

The term "RNA transcript" refers to the product resulting from RNA polymerase catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA" (mRNA) refers to the RNA that is without introns and that can be translated into protein by the cell. "cDNA" refers to a single- or a double-stranded DNA that is complementary to and derived from mRNA.

"Regulatory sequences" and "suitable regulatory sequences" each refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences that may be a combination of synthetic and natural sequences. As is noted above, the term "suitable regulatory sequences" is not limited to promoters. However, some suitable regulatory sequences useful in the present invention will include, but are not limited to constitutive promoters, tissue-specific promoters, development-specific promoters, regulatable promoters and viral promoters. Examples of promoters that may be used in the present invention include CMV, RSV, pol II and pol III promoters.

"5' non-coding sequence" refers to a nucleotide sequence located 5' (upstream) to the coding sequence. It is present in the fully processed mRNA upstream of the initiation codon and may affect processing of the primary transcript to mRNA, mRNA stability or translation efficiency.

"3' non-coding sequence" refers to nucleotide sequences located 3' (downstream) to a coding sequence and may include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor.

The term "translation leader sequence" refers to that DNA sequence portion of a gene between the promoter and coding sequence that is transcribed into RNA and is present in the fully processed mRNA upstream (5') of the translation start codon. The translation leader sequence may affect processing of the primary transcript to mRNA, mRNA stability or translation efficiency.

The term "mature" protein refers to a post-translationally processed polypeptide without its signal peptide. "Precursor" protein refers to the primary product of translation of an mRNA. "Signal peptide" refers to the amino terminal extension of a polypeptide, which is translated in conjunction with the polypeptide forming a precursor peptide and which is required for its entrance into the secretory pathway. The term "signal sequence" refers to a nucleotide sequence that encodes the signal peptide.

"Promoter" refers to a nucleotide sequence, usually upstream (5') to its coding sequence, which directs and/or controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions.

The "initiation site" is the position surrounding the first nucleotide that is part of the transcribed sequence, which is also defined as position +1. With respect to this site all other sequences of the gene and its controlling regions are numbered. Downstream sequences (i.e., further protein encoding sequences in the 3' direction) are denominated positive, while upstream sequences (mostly of the controlling regions in the 5' direction) are denominated negative.

Promoter elements, particularly a TATA element, that are inactive or that have greatly reduced promoter activity in the absence of upstream activation are referred to as "minimal or core promoters." In the presence of a suitable transcription factor, the minimal promoter functions to permit transcription. A "minimal or core promoter" thus consists only of all basal elements needed for transcription initiation, e.g., a TATA box and/or an initiator.

"Constitutive expression" refers to expression using a constitutive or regulated promoter. "Conditional" and "regulated expression" refer to expression controlled by a regulated promoter.

"Operably-linked" refers to the association of nucleic acid sequences on single nucleic acid fragment so that the function of one of the sequences is affected by another. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

"Expression" refers to the transcription and/or translation of an endogenous gene, heterologous gene or nucleic acid segment, or a transgene in cells. For example, in the case of RNAi molecule constructs, expression may refer to the transcription of the RNAi molecule only. In addition, expression refers to the transcription and stable accumulation of sense (mRNA) or functional RNA. Expression may also refer to the production of protein.

"Altered levels" refers to the level of expression in transgenic cells or organisms that differs from that of normal or untransformed cells or organisms.

"Overexpression" refers to the level of expression in transgenic cells or organisms that exceeds levels of expression in normal or untransformed cells or organisms.

"Antisense inhibition" refers to the production of antisense RNA transcripts capable of suppressing the expression of protein from an endogenous gene or a transgene.

"Transcription stop fragment" refers to nucleotide sequences that contain one or more regulatory signals, such as polyadenylation signal sequences, capable of terminating transcription. Examples include the 3' non-regulatory regions of genes encoding nopaline synthase and the small subunit of ribulose bisphosphate carboxylase.

"Translation stop fragment" refers to nucleotide sequences that contain one or more regulatory signals, such as one or more termination codons in all three frames, capable of terminating translation. Insertion of a translation stop fragment adjacent to or near the initiation codon at the 5' end of the coding sequence will result in no translation or improper translation. Excision of the translation stop fragment by site-specific recombination will leave a site-specific sequence in the coding sequence that does not interfere with proper translation using the initiation codon.

The terms "cis-acting sequence" and "cis-acting element" refer to DNA or RNA sequences whose functions require them to be on the same molecule. An example of a cis-acting sequence on the replicon is the viral replication origin.

The terms "trans-acting sequence" and "trans-acting element" refer to DNA or RNA sequences whose function does not require them to be on the same molecule.

"Chromosomally-integrated" refers to the integration of a foreign gene or nucleic acid construct into the host DNA by covalent bonds. Where genes are not "chromosomally integrated" they may be "transiently expressed." Transient expression of a gene refers to the expression of a gene that is not integrated into the host chromosome but functions independently, either as part of an autonomously replicating plasmid or expression cassette, for example, or as part of another biological system such as a virus.

The following terms are used to describe the sequence relationships between two or more nucleic acids or polynucleotides: (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well-known in the art. Thus, the determination of percent identity between any two sequences can be accomplished using a mathematical algorithm. Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well-known in the art.

Software for performing BLAST analyses is publicly available through the National Center for Biotechnology Information (see, the World-wide-web at ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, less than about 0.01, or even less than about 0.001.

To obtain gapped alignments for comparison purposes, Gapped BLAST (in BLAST 2.0) can be utilized. Alternatively, PSI-BLAST (in BLAST 2.0) can be used to perform an iterated search that detects distant relationships between molecules. When utilizing BLAST, Gapped BLAST, PSI-BLAST, the default parameters of the respective programs (e.g. BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See, the World-wide-web at ncbi.nlm.nih.gov). Alignment may also be performed manually by inspection.

For purposes of the present invention, comparison of nucleotide sequences for determination of percent sequence identity to the promoter sequences disclosed herein is made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70%, 71%, 72%, 73%, 74%, 75%, 76%, 77%, 78%, or 79%, or at least 80%, 81%, 82%, 83%, 84%, 85%, 86%, 87%, 88%, or 89%, or at least 90%, 91%, 92%, 93%, or 94%, or even at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, at least 80%, 90%, or even at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70%, 71%, 72%, 73%, 74%, 75%, 76%, 77%, 78%, or 79%, or 80%, 81%, 82%, 83%, 84%, 85%, 86%, 87%, 88%, or 89%, or at least 90%, 91%, 92%, 93%, or 94%, or even, 95%, 96%, 97%, 98% or 99%, sequence identity to the reference sequence over a specified comparison window. An indication that two peptide sequences are substantially identical is that one peptide is immunologically reactive with antibodies raised against the second peptide. Thus, a peptide is substantially identical to a second peptide, for example, where the two peptides differ only by a conservative substitution.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The $T_m$ is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl: $T_m$ 81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), the SSC concentration may be increased so that a higher temperature can be used. Generally, highly stringent hybridization and wash conditions are selected to be about 5° C. lower than the thermal melting point ($T_m$) for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes. Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.5 M, about 0.01 to 1.0 M, Na ion concentration (or other salts) at pH 7.0 to 8.3, and the temperature is typically at least about 30° C. and at least about 60° C. for long probes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

By "variant" polypeptide is intended a polypeptide derived from the native protein by deletion (also called "truncation") or addition of one or more amino acids to the N-terminal and/or C-terminal end of the native protein; deletion or addition of one or more amino acids at one or more sites in the native protein; or substitution of one or more amino acids at one or more sites in the native protein. Such variants may result from, for example, genetic polymorphism or from human manipulation. Methods for such manipulations are generally known in the art.

Thus, the polypeptides of the invention may be altered in various ways including amino acid substitutions, deletions, truncations, and insertions. Methods for such manipulations are generally known in the art. For example, amino acid sequence variants of the polypeptides can be prepared by mutations in the DNA. Methods for mutagenesis and nucleotide sequence alterations are well known in the art. Conservative substitutions, such as exchanging one amino acid with another having similar properties, may be used.

Thus, the genes and nucleotide sequences of the invention include both the naturally occurring sequences as well as variant forms. Likewise, the polypeptides of the invention encompass naturally-occurring proteins as well as variations and modified forms thereof. Such variants will continue to possess the desired activity. The deletions, insertions, and substitutions of the polypeptide sequence encompassed herein are not expected to produce radical changes in the characteristics of the polypeptide. However, when it is difficult to predict the exact effect of the substitution, deletion, or insertion in advance of doing so, one skilled in the art will appreciate that the effect will be evaluated by routine screening assays.

Individual substitutions deletions or additions that alter, add or delete a single amino acid or a small percentage of amino acids (typically less than 5%, more typically less than 1%) in an encoded sequence are "conservatively modified variations," where the alterations result in the substitution of an amino acid with a chemically similar amino acid. Conservative substitution tables providing functionally similar amino acids are well known in the art. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing:

Methionine (M), Cysteine (C); Basic: Arginine (R), Lysine (K), Histidine (H); Acidic: Aspartic acid (D), Glutamic acid (E), Asparagine (N), Glutamine (Q). In addition, individual substitutions, deletions or additions which alter, add or delete a single amino acid or a small percentage of amino acids in an encoded sequence are also "conservatively modified variations."

The term "transformation" refers to the transfer of a nucleic acid fragment into the genome of a host cell, resulting in genetically stable inheritance. A "host cell" is a cell that has been transformed, or is capable of transformation, by an exogenous nucleic acid molecule. Host cells containing the transformed nucleic acid fragments are referred to as "transgenic" cells, and organisms comprising transgenic cells are referred to as "transgenic organisms".

"Transformed," "transduced," "transgenic," and "recombinant" refer to a host cell or organism into which a heterologous nucleic acid molecule has been introduced. The nucleic acid molecule can be stably integrated into the genome generally known in the art. Known methods of PCR include, but are not limited to, methods using paired primers, nested primers, single specific primers, degenerate primers, gene-specific primers, vector-specific primers, partially mismatched primers, and the like. For example, "transformed," "transformant," and "transgenic" cells have been through the transformation process and contain a foreign gene integrated into their chromosome. The term "untransformed" refers to normal cells that have not been through the transformation process.

A "transgenic" organism is an organism having one or more cells that contain an expression vector.

"Genetically altered cells" denotes cells which have been modified by the introduction of recombinant or heterologous nucleic acids (e.g., one or more DNA constructs or their RNA counterparts) and further includes the progeny of such cells which retain part or all of such genetic modification.

The term "fusion protein" is intended to describe at least two polypeptides, typically from different sources, which are operably linked. With regard to polypeptides, the term operably linked is intended to mean that the two polypeptides are connected in a manner such that each polypeptide can serve its intended function. Typically, the two polypeptides are covalently attached through peptide bonds. The fusion protein is produced by standard recombinant DNA techniques. For example, a DNA molecule encoding the first polypeptide is ligated to another DNA molecule encoding the second polypeptide, and the resultant hybrid DNA molecule is expressed in a host cell to produce the fusion protein. The DNA molecules are ligated to each other in a 5' to 3' orientation such that, after ligation, the translational frame of the encoded polypeptides is not altered (i.e., the DNA molecules are ligated to each other in-frame).

As used herein, the term "derived" or "directed to" with respect to a nucleotide molecule means that the molecule has complementary sequence identity to a particular molecule of interest.

"Gene silencing" refers to the suppression of gene expression, e.g., transgene, heterologous gene and/or endogenous gene expression. Gene silencing may be mediated through processes that affect transcription and/or through processes that affect post-transcriptional mechanisms. In some embodiments, gene silencing occurs when RNAi molecule initiates the degradation of the mRNA of a gene of interest in a sequence-specific manner via RNA interference. In some embodiments, gene silencing may be allele-specific. "Allele-specific" gene silencing refers to the specific silencing of one allele of a gene.

"Knock-down," "knock-down technology" refers to a technique of gene silencing in which the expression of a target gene is reduced as compared to the gene expression prior to the introduction of the siRNA, which can lead to the inhibition of production of the target gene product. The term "reduced" is used herein to indicate that the target gene expression is lowered by 1-100%. For example, the expression may be reduced by 10, 20, 30, 40, 50, 60, 70, 80, 90, 95, or even 99%. Knock-down of gene expression can be directed by the use of dsRNAs or siRNAs. For example, "RNA interference (RNAi)," which can involve the use of an RNAi molecule, has been successfully applied to knockdown the expression of specific genes in plants, *D. melanogaster*, *C. elegans*, trypanosomes, planaria, hydra, and several vertebrate species including the mouse.

"RNA interference (RNAi)" is the process of sequence-specific, post-transcriptional gene silencing initiated by siRNA. RNAi is seen in a number of organisms such as *Drosophila*, nematodes, fungi and plants, and is believed to be involved in anti-viral defense, modulation of transposon activity, and regulation of gene expression. During RNAi, siRNA induces degradation of target mRNA with consequent sequence-specific inhibition of gene expression.

As used herein, the term siRNA is meant to be equivalent to other terms used to describe nucleic acid molecules that are capable of mediating sequence specific RNAi, for example, an RNAi molecule, double-stranded RNA (dsRNA), micro-RNA (miRNA), short hairpin RNA (shRNA), short interfering oligonucleotide, short interfering nucleic acid, post-transcriptional gene silencing RNA (ptgsRNA), and others. In addition, as used herein, the term RNAi is meant to be equivalent to other terms used to describe sequence specific RNA interference, such as post transcriptional gene silencing, translational inhibition, or epigenetic silencing. For example, siRNA molecules of the invention can be used to epigenetically silence genes at both the post-transcriptional level or the pre-transcriptional level. In a non-limiting example, epigenetic modulation of gene expression by siRNA molecules of the invention can result from siRNA mediated modification of chromatin structure or methylation pattern to alter gene expression. In another non-limiting example, modulation of gene expression by siRNA molecules of the invention can result from siRNA mediated cleavage of RNA (either coding or non-coding RNA) via RISC, or alternately, translational inhibition as is known in the art.

The RNAi molecule can be encoded by a nucleic acid sequence, and the nucleic acid sequence can also include a promoter. The nucleic acid sequence can also include a polyadenylation signal. In some embodiments, the polyadenylation signal is a synthetic minimal polyadenylation signal.

"Treating" as used herein refers to ameliorating at least one symptom of, curing and/or preventing the development of a disease or a condition.

"Neurological disease" and "neurological disorder" refer to both hereditary and sporadic conditions that are characterized by nervous system dysfunction, and which may be associated with atrophy of the affected central or peripheral nervous system structures, or loss of function without atrophy. A neurological disease or disorder that results in atrophy is commonly called a "neurodegenerative disease" or "neurodegenerative disorder." Neurodegenerative diseases and disorders include, but are not limited to, amyotrophic lateral sclerosis (ALS), hereditary spastic hemiplegia, primary lateral sclerosis, spinal muscular atrophy, Kennedy's disease, Alzheimer's disease, Parkinson's disease, multiple sclerosis, and repeat expansion neurodegenerative diseases, e.g., diseases associated with expansions of trinucleotide repeats such as polyglutamine (polyQ) repeat diseases, e.g., Huntington's disease (HD), spinocerebellar ataxia (SCA1, SCA2, SCA3, SCA6, SCA7, and SCA17), spinal and bulbar muscular atrophy (SBMA), dentatorubropallidoluysian atrophy (DRPLA). An example of a neurological disorder that does not appear to result in atrophy is DYT1 dystonia.

The siRNAs of the present invention can be generated by any method known to the art, for example, by in vitro transcription, recombinantly, or by synthetic means. In one example, the siRNAs can be generated in vitro by using a recombinant enzyme, such as T7 RNA polymerase, and DNA oligonucleotide templates.

II. Nucleic Acid Molecules of the Invention

Sources of nucleotide sequences from which the present nucleic acid molecules can be obtained include any vertebrate, such as mammalian, cellular source.

As discussed above, the terms "isolated and/or purified" refer to in vitro isolation of a nucleic acid, e.g., a DNA or RNA molecule from its natural cellular environment, and from association with other components of the cell, such as nucleic acid or polypeptide, so that it can be sequenced, replicated, and/or expressed. For example, "isolated nucleic acid" may be a DNA molecule containing less than 31 sequential nucleotides that is transcribed into an RNAi molecule. Such an isolated RNAi molecule may, for example, form a hairpin structure with a duplex 21 base pairs in length that is complementary or hybridizes to a sequence in a gene of interest, and remains stably bound under stringent conditions (as defined by methods well known in the art). Thus, the RNA or DNA is "isolated" in that it is free from at least one contaminating nucleic acid with which it is normally associated in the natural source of the RNA or DNA and is substantially free of any other mammalian RNA or DNA. The phrase "free from at least one contaminating source nucleic acid with which it is normally associated" includes the case where the nucleic acid is reintroduced into the source or natural cell but is in a different chromosomal location or is otherwise flanked by nucleic acid sequences not normally found in the source cell, e.g., in a vector or plasmid.

In addition to a DNA sequence encoding an RNAi molecule, the nucleic acid molecules of the invention include double-stranded interfering RNA molecules, which are also useful to inhibit expression of a target gene. In certain embodiment of the invention, siRNAs are employed to inhibit expression of a target gene. By "inhibit expression" is meant to reduce, diminish or suppress expression of a target gene. Expression of a target gene may be inhibited via "gene silencing." Gene silencing refers to the suppression of gene expression, e.g., transgene, heterologous gene and/or endogenous gene expression, which may be mediated through processes that affect transcription and/or through processes that affect post-transcriptional mechanisms. In some embodiments, gene silencing occurs when an RNAi molecule initiates the degradation of the mRNA transcribed from a gene of interest in a sequence-specific manner via RNA interference, thereby preventing translation of the gene's product.

As used herein, the term "recombinant nucleic acid", e.g., "recombinant DNA sequence or segment" refers to a nucleic acid, e.g., to DNA, that has been derived or isolated from any appropriate cellular source, that may be subsequently chemically altered in vitro, so that its sequence is not naturally occurring, or corresponds to naturally occurring sequences that are not positioned as they would be positioned in a genome which has not been transformed with exogenous DNA. An example of preselected DNA "derived" from a source, would be a DNA sequence that is identified as a useful fragment within a given organism, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

Thus, recovery or isolation of a given fragment of DNA from a restriction digest can employ separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. Therefore, "recombinant DNA" includes completely synthetic DNA sequences, semi-synthetic DNA sequences, DNA sequences isolated from biological sources, and DNA sequences derived from RNA, as well as mixtures thereof.

Nucleic acid molecules having base substitutions (i.e., variants) are prepared by a variety of methods known in the art. These methods include, but are not limited to, isolation from a natural source (in the case of naturally occurring sequence variants) or preparation by oligonucleotide-mediated (or site-directed) mutagenesis, PCR mutagenesis, and cassette mutagenesis of an earlier prepared variant or a non-variant version of the nucleic acid molecule.

Oligonucleotide-mediated mutagenesis is a method for preparing substitution variants. This technique is known in the art. Briefly, nucleic acid encoding an RNAi molecule can be altered by hybridizing an oligonucleotide encoding the desired mutation to a DNA template, where the template is the single-stranded form of a plasmid or bacteriophage containing the unaltered or native gene sequence. After hybridization, a DNA polymerase is used to synthesize an entire second complementary strand of the template that will thus incorporate the oligonucleotide primer, and will code for the selected alteration in the nucleic acid encoding the RNAi molecule. Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art.

The DNA template can be generated by those vectors that are either derived from bacteriophage M13 vectors (the commercially available M13 mp 18 and M13 mp 19 vectors are suitable), or those vectors that contain a single-stranded phage origin of replication. Thus, the DNA that is to be mutated may be inserted into one of these vectors to generate single-stranded template. Alternatively, single-stranded DNA template may be generated by denaturing double-stranded plasmid (or other) DNA using standard techniques.

For alteration of the native DNA sequence (to generate amino acid sequence variants, for example), the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form of the DNA, and the other strand (the original template) encodes the native, unaltered sequence of the DNA. This heteroduplex molecule is then transformed into a suitable host cell, usually a prokaryote such as *E. coli* JM101. After the cells are grown, they are plated onto agarose plates and screened using the oligonucleotide primer radiolabeled with 32-phosphate to identify the bacterial colonies that contain the mutated DNA. The mutated region is then removed and placed in an appropriate vector, generally an expression vector of the type typically employed for transformation of an appropriate host.

The method described immediately above may be modified such that a homoduplex molecule is created wherein both strands of the plasmid contain the mutations(s). The modifications are as follows: The single-stranded oligonucleotide is annealed to the single-stranded template as described above. A mixture of three deoxyribonucleotides, deoxyriboadenosine (dATP), deoxyriboguanosine (dGTP), and deoxyribothymidine (dTTP), is combined with a modified thiodeoxyribocytosine called dCTP-(*S) (which can be obtained from the Amersham Corporation). This mixture is added to the template-oligonucleotide complex. Upon addition of DNA polymerase to this mixture, a strand of DNA identical to the template except for the mutated bases is generated. In addition, this new strand of DNA will contain dCTP-(*S) instead of dCTP, which serves to protect it from restriction endonuclease digestion.

After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as E. coli JM101.

III. Expression Cassettes of the Invention

To prepare expression cassettes, the recombinant DNA sequence or segment may be circular or linear, double-stranded or single-stranded. Generally, the DNA sequence or segment is in the form of chimeric DNA, such as plasmid DNA or a vector that can also contain coding regions flanked by control sequences that promote the expression of the recombinant DNA present in the resultant transformed cell.

A "chimeric" vector or expression cassette, as used herein, means a vector or cassette including nucleic acid sequences from at least two different species, or has a nucleic acid sequence from the same species that is linked or associated in a manner that does not occur in the "native" or wild type of the species.

Aside from recombinant DNA sequences that serve as transcription units for an RNA transcript, or portions thereof, a portion of the recombinant DNA may be untranscribed, serving a regulatory or a structural function. For example, the recombinant DNA may have a promoter that is active in mammalian cells.

Other elements functional in the host cells, such as introns, enhancers, polyadenylation sequences and the like, may also be a part of the recombinant DNA. Such elements may or may not be necessary for the function of the DNA, but may provide improved expression of the DNA by affecting transcription, stability of the RNAi molecule, or the like. Such elements may be included in the DNA as desired to obtain the optimal performance of the RNAi molecule in the cell.

Control sequences are DNA sequences necessary for the expression of an operably linked coding sequence in a particular host organism. The control sequences that are suitable for prokaryotic cells, for example, include a promoter, and optionally an operator sequence, and a ribosome binding site. Eukaryotic cells are known to utilize promoters, polyadenylation signals, and enhancers.

Operably linked nucleic acids are nucleic acids placed in a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation. Generally, operably linked DNA sequences are DNA sequences that are linked are contiguous. However, enhancers do not have to be contiguous. Linking is accomplished by ligation at convenient restriction sites. If such sites do not exist, the synthetic oligonucleotide adaptors or linkers are used in accord with conventional practice.

The recombinant DNA to be introduced into the cells may contain either a selectable marker gene or a reporter gene or both to facilitate identification and selection of expressing cells from the population of cells sought to be transfected or infected through viral vectors. In other embodiments, the selectable marker may be carried on a separate piece of DNA and used in a co-transfection procedure. Both selectable markers and reporter genes may be flanked with appropriate regulatory sequences to enable expression in the host cells. Useful selectable markers are known in the art and include, for example, antibiotic-resistance genes, such as neo and the like.

Reporter genes are used for identifying potentially transfected cells and for evaluating the functionality of regulatory sequences. Reporter genes that encode for easily assayable proteins are well known in the art. In general, a reporter gene is a gene that is not present in or expressed by the recipient organism or tissue and that encodes a protein whose expression is manifested by some easily detectable property, e.g., enzymatic activity. For example, reporter genes include the chloramphenicol acetyl transferase gene (cat) from Tn9 of E. coli and the luciferase gene from firefly Photinus pyralis. Expression of the reporter gene is assayed at a suitable time after the DNA has been introduced into the recipient cells.

In order to prevent any packaging of AAV genomic sequences containing the rep and cap genes, a plasmid containing the rep and cap DNA fragment can be modified by the inclusion of a stuffer fragment into the AAV genome which causes the DNA to exceed the length for optimal packaging. Thus, in certain embodiments, the helper fragment is not packaged into AAV virions. This is a safety feature, ensuring that only a recombinant AAV vector genome that does not exceed optimal packaging size is packaged into virions. An AAV helper fragment that incorporates a stuffer sequence can exceed the wild-type genome length of 4.6 kb, and lengths above 105% of the wild-type will generally not be packaged. The stuffer fragment can be derived from, for example, such non-viral sources as the Lac-Z or beta-galactosidase gene.

The general methods for constructing recombinant DNA that can transfect target cells are well known to those skilled in the art, and the same compositions and methods of construction may be utilized to produce the DNA useful herein. The recombinant DNA can be readily introduced into the host cells, e.g., mammalian, bacterial, yeast or insect cells by transfection with an expression vector composed of DNA encoding the RNAi molecule by any procedure useful for the introduction into a particular cell, e.g., physical or biological methods, to yield a cell having the recombinant DNA stably integrated into its genome or existing as a episomal element, so that the DNA molecules, or sequences of the present invention are expressed by the host cell. The DNA is introduced into host cells via a vector. The host cell is may be of eukaryotic origin, e.g., plant, mammalian, insect, yeast or fungal sources, but host cells of non-eukaryotic origin may also be employed.

Physical methods to introduce a preselected DNA into a host cell include calcium phosphate precipitation, lipofection, particle bombardment, microinjection, electroporation, and the like. Biological methods to introduce the DNA of interest into a host cell include the use of DNA and RNA viral vectors. For mammalian gene therapy, as described hereinbelow, it is desirable to use an efficient means of inserting a copy gene into the host genome. Viral vectors, and especially retroviral vectors, have become the most widely used method for inserting genes into mammalian, e.g., human cells. Other viral vectors can be derived from poxviruses, herpes simplex virus I, adenoviruses and adeno-associated viruses, and the like.

As discussed above, a "transfected," "or "transduced" host cell or cell line is one in which the genome has been altered or augmented by the presence of at least one heterologous or recombinant nucleic acid sequence. The host cells of the present invention are typically produced by transfection with a DNA sequence in a plasmid expression vector, a viral expression vector, or as an isolated linear DNA sequence. The transfected DNA can become a chromosomally integrated recombinant DNA sequence, which is composed of sequence encoding the RNAi molecule.

To confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

To detect and quantitate RNA produced from introduced recombinant DNA segments, RT-PCR may be employed. In this application of PCR, it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique demonstrates the presence of an RNA species and gives information about the integrity of that RNA. The presence or absence of an RNA species can also be determined using dot or slot blot Northern hybridizations. These techniques are modifications of Northern blotting and only demonstrate the presence or absence of an RNA species.

While Southern blotting and PCR may be used to detect the recombinant DNA segment in question, they do not provide information as to whether the preselected DNA segment is being expressed. Expression may be evaluated by specifically identifying the peptide products of the introduced recombinant DNA sequences or evaluating the phenotypic changes brought about by the expression of the introduced recombinant DNA segment in the host cell.

The instant invention provides a cell expression system for expressing exogenous nucleic acid material in a mammalian recipient. The expression system, also referred to as a "genetically modified cell," comprises a cell and an expression vector for expressing the exogenous nucleic acid material. The genetically modified cells are suitable for administration to a mammalian recipient, where they replace the endogenous cells of the recipient. Thus, the genetically modified cells are non-immortalized and are non-tumorigenic.

According to one embodiment, the cells are transfected or otherwise genetically modified ex vivo. The cells are isolated from a mammal (such as a human), nucleic acid introduced (i.e., transduced or transfected in vitro) with a vector for expressing a heterologous (e.g., recombinant) gene encoding the therapeutic agent, and then administered to a mammalian recipient for delivery of the therapeutic agent in situ. The mammalian recipient may be a human and the cells to be modified are autologous cells, i.e., the cells are isolated from the mammalian recipient.

According to another embodiment, the cells are transfected or transduced or otherwise genetically modified in vivo. The cells from the mammalian recipient are transduced or transfected in vivo with a vector containing exogenous nucleic acid material for expressing a heterologous (e.g., recombinant) gene encoding a therapeutic agent and the therapeutic agent is delivered in situ.

As used herein, "exogenous nucleic acid material" refers to a nucleic acid or an oligonucleotide, either natural or synthetic, which is not naturally found in the cells; or if it is naturally found in the cells, is modified from its original or native form. Thus, "exogenous nucleic acid material" includes, for example, a non-naturally occurring nucleic acid that can be transcribed into an anti-sense RNA, an RNAi molecule, as well as a "heterologous gene" (i.e., a gene encoding a protein that is not expressed or is expressed at biologically insignificant levels in a naturally-occurring cell of the same type). To illustrate, a synthetic or natural gene encoding human erythropoietin (EPO) would be considered "exogenous nucleic acid material" with respect to human peritoneal mesothelial cells since the latter cells do not naturally express EPO. Still another example of "exogenous nucleic acid material" is the introduction of only part of a gene to create a recombinant gene, such as combining a regulatable promoter with an endogenous coding sequence via homologous recombination.

IV. Promoters and Expression Vectors of the Invention

As described herein, an expression cassette of the invention contains, inter alia, a promoter. Such promoters include the CMV promoter, as well as the RSV promoter, SV40 late promoter and retroviral LTRs (long terminal repeat elements), or brain cell specific promoters, although many other promoter elements well known to the art, such as tissue specific promoters or regulatable promoters may be employed in the practice of the invention.

In one embodiment of the present invention, an expression cassette may contain a pol II promoter that is operably linked to a nucleic acid sequence encoding an RNAi molecule. Thus, the pol II promoter, i.e., a RNA polymerase II dependent promoter, initiates the transcription of the RNAi molecule. In another embodiment, the pol II promoter is regulatable.

Three RNA polymerases transcribe nuclear genes in eukaryotes. RNA polymerase II (pol II) synthesizes mRNA, i.e., pol II transcribes the genes that encode proteins. In contrast, RNA polymerase I (pol I) and RNA polymerase III (pol III) transcribe only a limited set of transcripts, synthesizing RNAs that have structural or catalytic roles. RNA polymerase I makes the large ribosomal RNAs (rRNA), which are under the control of pol I promoters. RNA polymerase III makes a variety of small, stable RNAs, including the small 5S rRNA and transfer RNAs (tRNA), the transcription of which is under the control of pol III promoters.

As described herein, the inventors unexpectedly discovered that pol II promoters are useful to direct transcription of the siRNA. This was surprising because, as discussed above, pol II promoters are thought to be responsible for transcription of messenger RNA, i.e., relatively long RNAs as compared to RNAs of 30 bases or less.

A pol II promoter may be used in its entirety, or a portion or fragment of the promoter sequence may be used in which the portion maintains the promoter activity. As discussed herein, pol II promoters are known to a skilled person in the art and include the promoter of any protein-encoding gene, e.g., an endogenously regulated gene or a constitutively expressed gene. For example, the promoters of genes regulated by cellular physiological events, e.g., heat shock, oxygen levels and/or carbon monoxide levels, e.g., in hypoxia, may be used in the expression cassettes of the invention. In addition, the promoter of any gene regulated by the presence of a pharmacological agent, e.g., tetracycline and derivatives thereof, as well as heavy metal ions and hormones may be employed in the expression cassettes of the invention. In an embodiment of the invention, the pol II promoter can be the CMV promoter or the RSV promoter. In another embodiment, the pol II promoter is the CMV promoter.

As discussed above, a pol II promoter of the invention may be one naturally associated with an endogenously regulated gene or sequence, as may be obtained by isolating the 5' non-coding sequences located upstream of the coding segment and/or exon. The pol II promoter of the expression cassette can be, for example, the same pol II promoter driving expression of the targeted gene of interest. Alternatively, the nucleic acid sequence encoding the siRNA may be placed under the control of a recombinant or heterologous pol II promoter, which refers to a promoter that is not normally associated with the targeted gene's natural environment. Such promoters include promoters isolated from any eukaryotic cell, and promoters not "naturally occurring," i.e., containing different elements of different transcriptional regulatory regions, and/or mutations that alter expression. In addition to producing nucleic acid sequences of promoters synthetically, sequences may be produced using recombinant cloning and/or nucleic acid amplification technology, including PCR™, in connection with the compositions disclosed herein (see U.S. Pat. No. 4,683,202, U.S. Pat. No. 5,928,906, each incorporated herein by reference).

In one embodiment, a pol II promoter that effectively directs the expression of the siRNA in the cell type, organelle, and organism chosen for expression will be employed. Those of ordinary skill in the art of molecular biology generally know the use of promoters for protein expression. The promoters employed may be constitutive, tissue-specific, inducible, and/or useful under the appropriate conditions to direct high level expression of the introduced DNA segment, such as is advantageous in the large-scale production of recombinant proteins and/or peptides. The identity of tissue-specific promoters, as well as assays to characterize their activity, is well known to those of ordinary skill in the art.

In another aspect of the invention, RNA molecules of the present invention can be expressed from transcription units inserted into DNA or RNA vectors. The recombinant vectors can be DNA plasmids or viral vectors. siRNA expressing viral vectors can be constructed based on, but not limited to, adeno-associated virus, retrovirus, adenovirus, or alphavirus. In another embodiment, pol III based constructs are used to express nucleic acid molecules of the invention. The recombinant vectors capable of expressing the RNAi molecule can be delivered as described above, and persist in target cells. Alternatively, viral vectors can be used that provide for transient expression of nucleic acid molecules. Such vectors can be repeatedly administered as necessary. Once expressed, the RNAi molecule interacts with the target mRNA and generates an RNAi response. Delivery of RNAi molecule-expressing vectors can be systemic, such as by intravenous or intramuscular administration, by administration to target cells ex-planted from a subject followed by reintroduction into the subject, or by any other means that would allow for introduction into the desired target cell. In one aspect the invention features an expression vector comprising a nucleic acid sequence encoding at least one RNAi molecule of the instant invention. The expression vector can encode one or both strands of a RNAi molecule duplex, or a single self-complementary strand that self hybridizes into a RNAi molecule duplex. The nucleic acid sequences encoding the RNAi molecules of the instant invention can be operably linked in a manner that allows expression of the RNAi molecule.

In another aspect, the invention features an expression vector comprising: a) a transcription initiation region (e.g., eukaryotic pol I, II or III initiation region); b) a transcription termination region (e.g., eukaryotic pol I, II or III termination region); and c) a nucleic acid sequence encoding at least one of the siRNA molecules of the instant invention, wherein said sequence is operably linked to said initiation region and said termination region in a manner that allows expression and/or delivery of the RNAi molecule. The vector can optionally include an open reading frame (ORF) for a protein operably linked on the 5' side or the 3'-side of the sequence encoding the RNAi molecule of the invention; and/or an intron (intervening sequences).

Transcription of the RNAi molecule sequences can be driven from a promoter for eukaryotic RNA polymerase I (pol I), RNA polymerase II (pol II), or RNA polymerase III (pol III). Transcripts from pol II or pol III promoters are expressed at high levels in all cells; the levels of a given pol II promoter in a given cell type depends on the nature of the gene regulatory sequences (enhancers, silencers, etc.) present nearby. Prokaryotic RNA polymerase promoters are also used, providing that the prokaryotic RNA polymerase enzyme is expressed in the appropriate cells. Several investigators have demonstrated that nucleic acid molecules expressed from such promoters can function in mammalian cells. More specifically, transcription units such as the ones derived from genes encoding U6 small nuclear (snRNA), transfer RNA (tRNA) and adenovirus VA RNA are useful in generating high concentrations of desired RNA molecules such as RNAi molecule in cells. The above RNAi molecule transcription units can be incorporated into a variety of vectors for introduction into mammalian cells, including but not restricted to, plasmid DNA vectors, viral DNA vectors (such as adenovirus or adeno-associated virus vectors), or viral RNA vectors (such as retroviral or alphavirus vectors).

In another aspect the invention features an expression vector comprising a nucleic acid sequence encoding at least one of the RNAi molecules of the invention in a manner that allows expression of that RNAi molecule. The expression vector comprises in one embodiment; a) a transcription initiation region; b) a transcription termination region; and c) a nucleic acid sequence encoding at least one strand of the RNAi molecule, wherein the sequence is operably linked to the initiation region and the termination region in a manner that allows expression and/or delivery of the RNAi molecule.

In another embodiment the expression vector comprises: a) a transcription initiation region; b) a transcription termination region; c) an open reading frame; and d) a nucleic acid sequence encoding at least one strand of a RNAi molecule, wherein the sequence is operably linked to the 3'-end of the open reading frame and wherein the sequence is operably linked to the initiation region, the open reading frame and the termination region in a manner that allows expression and/or delivery of the RNAi molecule. In yet another embodiment, the expression vector comprises: a) a transcription initiation region; b) a transcription termination region; c) an intron; and d) a nucleic acid sequence encoding at least one RNAi molecule, wherein the sequence is operably linked to the initiation region, the intron and the termination region in a manner which allows expression and/or delivery of the nucleic acid molecule.

In another embodiment, the expression vector comprises: a) a transcription initiation region; b) a transcription termination region; c) an intron; d) an open reading frame; and e) a nucleic acid sequence encoding at least one strand of a RNAi molecule, wherein the sequence is operably linked to the 3'-end of the open reading frame and wherein the sequence is operably linked to the initiation region, the intron, the open reading frame and the termination region in a manner which allows expression and/or delivery of the RNAi molecule.

V. Methods for Introducing the Expression Cassettes of the Invention into Cells

The condition amenable to gene inhibition therapy may be a prophylactic process, i.e., a process for preventing disease or an undesired medical condition. Thus, the instant invention embraces a system for delivering RNAi molecules that has a prophylactic function (i.e., a prophylactic agent) to the mammalian recipient.

The inhibitory nucleic acid material (e.g., an expression cassette encoding RNAi molecules directed to a gene of interest) can be introduced into the cell ex vivo or in vivo by genetic transfer methods, such as transfection or transduction, to provide a genetically modified cell. Various expression vectors (i.e., vehicles for facilitating delivery of exogenous nucleic acid into a target cell) are known to one of ordinary skill in the art.

As used herein, "transfection of cells" refers to the acquisition by a cell of new nucleic acid material by incorporation of added DNA. Thus, transfection refers to the insertion of nucleic acid into a cell using physical or chemical methods. Several transfection techniques are known to those of ordinary skill in the art including: calcium phosphate DNA coprecipitation; DEAE-dextran; electroporation; cationic liposome-mediated transfection; and tungsten particle-facilitated microparticle bombardment. Strontium phosphate DNA coprecipitation is also a transfection method.

In contrast, "transduction of cells" refers to the process of transferring nucleic acid into a cell using a DNA or RNA virus. A RNA virus (i.e., a retrovirus) for transferring a nucleic acid into a cell is referred to herein as a transducing chimeric retrovirus. Exogenous nucleic acid material contained within the retrovirus is incorporated into the genome of the transduced cell. A cell that has been transduced with a chimeric DNA virus (e.g., an adenovirus carrying a cDNA encoding a therapeutic agent), will not have the exogenous nucleic acid material incorporated into its genome but will be capable of expressing the exogenous nucleic acid material that is retained extrachromosomally within the cell.

The exogenous nucleic acid material can include the nucleic acid encoding the RNAi molecule together with a promoter to control transcription. The promoter characteristically has a specific nucleotide sequence necessary to initiate transcription. The exogenous nucleic acid material may further include additional sequences (i.e., enhancers) required to obtain the desired gene transcription activity. For the purpose of this discussion an "enhancer" is simply any non-translated DNA sequence that works with the coding sequence (in cis) to change the basal transcription level dictated by the promoter. The exogenous nucleic acid material may be introduced into the cell genome immediately downstream from the promoter so that the promoter and coding sequence are operatively linked so as to permit transcription of the coding sequence. An expression vector can include an exogenous promoter element to control transcription of the inserted exogenous gene. Such exogenous promoters include both constitutive and regulatable promoters.

Naturally-occurring constitutive promoters control the expression of essential cell functions. As a result, a nucleic acid sequence under the control of a constitutive promoter is expressed under all conditions of cell growth. Constitutive promoters include the promoters for the following genes which encode certain constitutive or "housekeeping" functions: hypoxanthine phosphoribosyl transferase (HPRT), dihydrofolate reductase (DHFR), adenosine deaminase, phosphoglycerol kinase (PGK), pyruvate kinase, phosphoglycerol mutase, the beta☐-actin promoter, and other constitutive promoters known to those of skill in the art. In addition, many viral promoters function constitutively in eukaryotic cells. These include: the early and late promoters of SV40; the long terminal repeats (LTRs) of Moloney Leukemia Virus and other retroviruses; and the thymidine kinase promoter of Herpes Simplex Virus, among many others.

Nucleic acid sequences that are under the control of regulatable promoters are expressed only or to a greater or lesser degree in the presence of an inducing or repressing agent, (e.g., transcription under control of the metallothionein promoter is greatly increased in presence of certain metal ions). Regulatable promoters include responsive elements (REs) that stimulate transcription when their inducing factors are bound. For example, there are REs for serum factors, steroid hormones, retinoic acid, cyclic AMP, and tetracycline and doxycycline. Promoters containing a particular RE can be chosen in order to obtain an regulatable response and in some cases, the RE itself may be attached to a different promoter, thereby conferring regulatability to the encoded nucleic acid sequence. Thus, by selecting the appropriate promoter (constitutive versus regulatable; strong versus weak), it is possible to control both the existence and level of expression of a nucleic acid sequence in the genetically modified cell. If the nucleic acid sequence is under the control of an regulatable promoter, delivery of the therapeutic agent in situ is triggered by exposing the genetically modified cell in situ to conditions for permitting transcription of the nucleic acid sequence, e.g., by intraperitoneal injection of specific inducers of the regulatable promoters which control transcription of the agent. For example, in situ expression of a nucleic acid sequence under the control of the metallothionein promoter in genetically modified cells is enhanced by contacting the genetically modified cells with a solution containing the appropriate (i.e., inducing) metal ions in situ.

Accordingly, the amount of RNAi molecules generated in situ is regulated by controlling such factors as the nature of the promoter used to direct transcription of the nucleic acid sequence, (i.e., whether the promoter is constitutive or regulatable, strong or weak) and the number of copies of the exogenous nucleic acid sequence encoding a RNAi molecule sequence that are in the cell.

In addition to at least one promoter and at least one heterologous nucleic acid sequence encoding the RNAi molecule, the expression vector may include a selection gene, for example, a neomycin resistance gene, for facilitating selection of cells that have been transfected or transduced with the expression vector.

Cells can also be transfected with two or more expression vectors, at least one vector containing the nucleic acid sequence(s) encoding the RNAi molecule(s), the other vector containing a selection gene. The selection of a suitable promoter, enhancer, selection gene and/or signal sequence is deemed to be within the scope of one of ordinary skill in the art without undue experimentation.

The following discussion is directed to various utilities of the instant invention. For example, the instant invention has utility as an expression system suitable for silencing the expression of gene(s) of interest.

The instant invention also provides various methods for making and using the above-described genetically-modified cells.

The instant invention also provides methods for genetically modifying cells of a mammalian recipient in vivo. According to one embodiment, the method comprises introducing an expression vector for expressing a RNAi molecule sequence in cells of the mammalian recipient in situ by, for example, injecting the vector into the recipient.

VI. Delivery Vehicles for the Expression Cassettes of the Invention

Delivery of compounds into tissues and across the blood-brain barrier can be limited by the size and biochemical properties of the compounds. Currently, efficient delivery of compounds into cells in vivo can be achieved only when the molecules are small (usually less than 600 Daltons). Gene transfer for the correction of inborn errors of metabolism and neurodegenerative diseases of the central nervous system (CNS), and for the treatment of cancer has been accomplished with recombinant adenoviral vectors.

The selection and optimization of a particular expression vector for expressing a specific RNAi molecules in a cell can be accomplished by obtaining the nucleic acid sequence of the RNAi molecule, possibly with one or more appropriate control regions (e.g., promoter, insertion sequence); preparing a vector construct comprising the vector into which is inserted the nucleic acid sequence encoding the RNAi molecule; transfecting or transducing cultured cells in vitro with the vector construct; and determining whether the RNAi molecule is present in the cultured cells.

Vectors for cell gene therapy include viruses, such as replication-deficient viruses (described in detail below). Exemplary viral vectors are derived from Harvey Sarcoma virus, ROUS Sarcoma virus, (MPSV), Moloney murine leukemia virus and DNA viruses (e.g., adenovirus).

Replication-deficient retroviruses are capable of directing synthesis of all virion proteins, but are incapable of making infectious particles. Accordingly, these genetically altered retroviral expression vectors have general utility for high-efficiency transduction of nucleic acid sequences in cultured cells, and specific utility for use in the method of the present invention. Such retroviruses further have utility for the efficient transduction of nucleic acid sequences into cells in vivo. Retroviruses have been used extensively for transferring nucleic acid material into cells. Standard protocols for producing replication-deficient retroviruses (including the steps of incorporation of exogenous nucleic acid material into a plasmid, transfection of a packaging cell line with plasmid, production of recombinant retroviruses by the packaging cell line, collection of viral particles from tissue culture media, and infection of the target cells with the viral particles) are well known in the art.

An advantage of using retroviruses for gene therapy is that the viruses insert the nucleic acid sequence encoding the RNAi molecule into the host cell genome, thereby permitting the nucleic acid sequence encoding the RNAi molecule to be passed on to the progeny of the cell when it divides. Promoter sequences in the LTR region have been reported to enhance expression of an inserted coding sequence in a variety of cell types. Some disadvantages of using a retrovirus expression vector are (1) insertional mutagenesis, i.e., the insertion of the nucleic acid sequence encoding the RNAi molecule into an undesirable position in the target cell genome which, for example, leads to unregulated cell growth and (2) the need for target cell proliferation in order for the nucleic acid sequence encoding the RNAi molecule carried by the vector to be integrated into the target genome.

Another viral candidate useful as an expression vector for transformation of cells is the adenovirus, a double-stranded DNA virus. The adenovirus is infective in a wide range of cell types, including, for example, muscle and endothelial cells. The adenovirus also has been used as an expression vector in muscle cells in vivo.

Adenoviruses (Ad) are double-stranded linear DNA viruses with a 36 kb genome. Several features of adenovirus have made them useful as transgene delivery vehicles for therapeutic applications, such as facilitating in vivo gene delivery. Recombinant adenovirus vectors have been shown to be capable of efficient in situ gene transfer to parenchymal cells of various organs, including the lung, brain, pancreas, gallbladder, and liver. This has allowed the use of these vectors in methods for treating inherited genetic diseases, such as cystic fibrosis, where vectors may be delivered to a target organ. In addition, the ability of the adenovirus vector to accomplish in situ tumor transduction has allowed the development of a variety of anticancer gene therapy methods for non-disseminated disease. In these methods, vector containment favors tumor cell-specific transduction.

Like the retrovirus, the adenovirus genome is adaptable for use as an expression vector for gene therapy, i.e., by removing the genetic information that controls production of the virus itself. Because the adenovirus functions in an extrachromosomal fashion, the recombinant adenovirus does not have the theoretical problem of insertional mutagenesis.

Several approaches traditionally have been used to generate the recombinant adenoviruses. One approach involves direct ligation of restriction endonuclease fragments containing a nucleic acid sequence of interest to portions of the adenoviral genome. Alternatively, the nucleic acid sequence of interest may be inserted into a defective adenovirus by homologous recombination results. The desired recombinants are identified by screening individual plaques generated in a lawn of complementation cells.

Most adenovirus vectors are based on the adenovirus type 5 (Ad5) backbone in which an expression cassette containing the nucleic acid sequence of interest has been introduced in place of the early region 1 (E1) or early region 3 (E3). Viruses in which E1 has been deleted are defective for replication and are propagated in human complementation cells (e.g., 293 or 911 cells), which supply the missing gene E1 and pIX in trans.

In one embodiment of the present invention, one will desire to generate siRNA in a brain cell or brain tissue. A suitable vector for this application is an FIV vector or an AAV vector. For example, one may use AAV5. Also, one may apply poliovirus or HSV vectors.

Adeno associated virus (AAV) is a small nonpathogenic virus of the parvoviridae family. AAV is distinct from the other members of this family by its dependence upon a helper virus for replication. In the absence of a helper virus, AAV may integrate in a locus specific manner into the q arm of chromosome 19. The approximately 5 kb genome of AAV consists of one segment of single stranded DNA of either plus or minus polarity. The ends of the genome are short inverted terminal repeats which can fold into hairpin structures and serve as the origin of viral DNA replication. Physically, the parvovirus virion is non-enveloped and its icosahedral capsid is approximately 20 nm in diameter.

To-date seven serologically distinct AAVs have been identified and five have been isolated from humans or primates and are referred to as AAV types 1-5. The most extensively studied of these isolates is AAV type 2 (AAV2). The genome of AAV2 is 4680 nucleotides in length and contains two open reading frames (ORFs). The left ORF encodes the non-structural Rep proteins, Rep40, Rep 52, Rep68 and Rep 78, which are involved in regulation of replication and transcription in addition to the production of single-stranded progeny genomes. Furthermore, two of the Rep proteins have been associated with the possible integration of AAV genomes into a region of the q arm of human chromosome 19. Rep68/78 have also been shown to possess NTP binding activity as well as DNA and RNA helicase activities. The Rep proteins possess a nuclear localization signal as well as several potential phosphorylation sites. Mutation of one of these kinase sites resulted in a loss of replication activity.

The ends of the genome are short inverted terminal repeats which have the potential to fold into T-shaped hairpin structures that serve as the origin of viral DNA replication. Within the ITR region two elements have been described which are central to the function of the ITR, a GAGC repeat motif and the terminal resolution site (trs). The repeat motif has been shown to bind Rep when the ITR is in either a linear or hairpin conformation. This binding serves to position Rep68/78 for cleavage at the trs which occurs in a site- and strand-specific manner. In addition to their role in replication, these two elements appear to be central to viral integration. Contained within the chromosome 19 integration locus is a Rep binding site with an adjacent trs. These elements have been shown to be functional and necessary for locus specific integration.

The AAV2 virion is a non-enveloped, icosohedral particle approximately 25 nm in diameter, consisting of three related proteins referred to as VPI, 2 and 3. The right ORF encodes the capsid proteins, VP1, VP2, and VP3. These proteins are found in a ratio of 1:1:10 respectively and are all derived from the right-hand ORF. The capsid proteins differ from each other by the use of alternative splicing and an unusual start codon. Deletion analysis has shown that removal or alteration of VP1 which is translated from an alternatively spliced message results in a reduced yield of infections particles. Mutations within the VP3 coding region result in the failure to produce any single-stranded progeny DNA or infectious particles.

The following features of AAV have made it an attractive vector for gene transfer. AAV vectors have been shown in vitro to stably integrate into the cellular genome; possess a broad host range; transduce both dividing and non dividing cells in vitro and in vivo and maintain high levels of expression of the transduced genes. Viral particles are heat stable, resistant to solvents, detergents, changes in pH, temperature, and can be concentrated on CsCl gradients. Integration of AAV provirus is not associated with any long term negative effects on cell growth or differentiation. The ITRs have been shown to be the only cis elements required for replication, packaging and integration and may contain some promoter activities.

Further provided by this invention are chimeric viruses where AAV can be combined with herpes virus, herpes virus amplicons, baculovirus or other viruses to achieve a desired tropism associated with another virus. For example, the AAV4 ITRs could be inserted in the herpes virus and cells could be infected. Post-infection, the ITRs of AAV4 could be acted on by AAV4 rep provided in the system or in a separate vehicle to rescue AAV4 from the genome. Therefore, the cellular tropism of the herpes simplex virus can be combined with AAV4 rep mediated targeted integration. Other viruses that could be utilized to construct chimeric viruses include lentivirus, retrovirus, pseudotyped retroviral vectors, and adenoviral vectors.

Also provided by this invention are variant AAV vectors. For example, the sequence of a native AAV, such as AAV5, can be modified at individual nucleotides. The present invention includes native and mutant AAV vectors. The present invention further includes all AAV serotypes.

Thus, as will be apparent to one of ordinary skill in the art, a variety of suitable viral expression vectors are available for transferring exogenous nucleic acid material into cells. The selection of an appropriate expression vector to express a therapeutic agent for a particular condition amenable to gene silencing therapy and the optimization of the conditions for insertion of the selected expression vector into the cell, are within the scope of one of ordinary skill in the art without the need for undue experimentation.

In another embodiment, the expression vector is in the form of a plasmid, which is transferred into the target cells by one of a variety of methods: physical (e.g., microinjection, electroporation, scrape loading, microparticle bombardment) or by cellular uptake as a chemical complex (e.g., calcium or strontium co-precipitation, complexation with lipid, complexation with ligand). Several commercial products are available for cationic liposome complexation including Lipofectin™ (Gibco-BRL, Gaithersburg, Md.) and Transfectam™ (Promega, Madison, Wis.). However, the efficiency of transfection by these methods is highly dependent on the nature of the target cell and accordingly, the conditions for optimal transfection of nucleic acids into cells using the above-mentioned procedures must be optimized. Such optimization is within the scope of one of ordinary skill in the art without the need for undue experimentation.

VII. Diseases and Conditions Amendable to the Methods of the Invention

In the certain embodiments of the present invention, a mammalian recipient to an expression cassette of the invention has a condition that is amenable to gene silencing therapy. As used herein, "gene silencing therapy" refers to administration to the recipient exogenous nucleic acid material encoding a therapeutic siRNA and subsequent expression of the administered nucleic acid material in situ. Thus, the phrase "condition amenable to RNAi molecule therapy" embraces conditions such as genetic diseases (i.e., a disease condition that is attributable to one or more gene defects), acquired pathologies (i.e., a pathological condition that is not attributable to an inborn defect), cancers, neurodegenerative diseases, e.g., trinucleotide repeat disorders, and prophylactic processes (i.e., prevention of a disease or of an undesired medical condition). A gene "associated with a condition" is a gene that is either the cause, or is part of the cause, of the condition to be treated. Examples of such genes include genes associated with a neurodegenerative disease (e.g., a trinucleotide-repeat disease such as a disease associated with polyglutamine repeats, Huntington's disease, and several spinocerebellar ataxias), and genes encoding ligands for chemokines involved in the migration of a cancer cells, or chemokine receptor. Also RNAi molecules expressed from viral vectors may be used for in vivo antiviral therapy using the vector systems described.

Accordingly, as used herein, the term "therapeutic siRNA" refers to any siRNA that has a beneficial effect on the recipient. Thus, "therapeutic siRNA" embraces both therapeutic and prophylactic siRNA.

Differences between alleles that are amenable to targeting by siRNA include disease-causing mutations as well as polymorphisms that are not themselves mutations, but may be linked to a mutation or associated with a predisposition to a disease state. Examples of targetable disease mutations include tau mutations that cause frontotemporal dementia and the GAG deletion in the TOR1A gene that causes DYT1 dystonia. An example of a targetable polymorphism that is not itself a mutation is the C/G single nucleotide polymorphism (G987C) in the MJD1 gene immediately downstream of the mutation that causes spinocerebellar ataxia type 3 and the polymorphism in exon 58 associated with Huntington's disease.

Single nucleotide polymorphisms comprise most of the genetic diversity between humans, and that many disease genes, including the HD gene in Huntington's disease, contain numerous single nucleotide or multiple nucleotide polymorphisms that could be separately targeted in one allele vs. the other. The major risk factor for developing Alzheimer's disease is the presence of a particular polymorphism in the apolipoprotein E gene.

A. Gene Defects

A number of diseases caused by gene defects have been identified. For example, this strategy can be applied to a major class of disabling neurological disorders. For example this strategy can be applied to the polyglutamine diseases, as is demonstrated by the reduction of polyglutamine aggregation in cells following application of the strategy. The neurodegenerative disease may be a trinucleotide-repeat disease, such as a disease associated with polyglutamine repeats, including Huntington's disease, and several spinocerebellar ataxias. Additionally, this strategy can be applied to a non-degenerative neurological disorder, such as DYT1 dystonia.

B. Acquired Pathologies

As used herein, "acquired pathology" refers to a disease or syndrome manifested by an abnormal physiological, biochemical, cellular, structural, or molecular biological state. For example, the disease could be a viral disease, such as hepatitis or AIDS.

C. Cancers

The condition amenable to gene silencing therapy alternatively can be a genetic disorder or an acquired pathology that is manifested by abnormal cell proliferation, e.g., cancer. According to this embodiment, the instant invention is useful for silencing a gene involved in neoplastic activity. The present invention can also be used to inhibit overexpression of one or several genes. The present invention can be used to treat neuroblastoma, medulloblastoma, or glioblastoma.

VIII. Dosages, Formulations and Routes of Administration of the Agents of the Invention The agents of the invention are administered so as to result in a reduction in at least one symptom associated with a disease. The amount administered will vary depending on various factors including, but not limited to, the composition chosen, the particular disease, the weight, the physical condition, and the age of the mammal, and whether prevention or treatment is to be achieved. Such factors can be readily determined by the clinician employing animal models or other test systems which are well known to the art.

Administration of siRNA may be accomplished through the administration of the nucleic acid molecule encoding the siRNA. Pharmaceutical formulations, dosages and routes of administration for nucleic acids are generally well known in the art.

The present invention envisions treating a disease, for example, a neurodegenerative disease, in a mammal by the administration of an agent, e.g., a nucleic acid composition, an expression vector, or a viral particle of the invention. Administration of the therapeutic agents in accordance with the present invention may be continuous or intermittent, depending, for example, upon the recipient's physiological condition, whether the purpose of the administration is therapeutic or prophylactic, and other factors known to skilled practitioners. The administration of the agents of the invention may be essentially continuous over a preselected period of time or may be in a series of spaced doses. Both local and systemic administration is contemplated.

One or more suitable unit dosage forms having the therapeutic agent(s) of the invention, which, as discussed below, may optionally be formulated for sustained release (for example using microencapsulation), can be administered by a variety of routes including parenteral, including by intravenous and intramuscular routes, as well as by direct injection into the diseased tissue. For example, the therapeutic agent may be directly injected into the brain. Alternatively the therapeutic agent may be introduced intrathecally for brain and spinal cord conditions. In another example, the therapeutic agent may be introduced intramuscularly for viruses that traffic back to affected neurons from muscle, such as AAV, lentivirus and adenovirus. The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

When the therapeutic agents of the invention are prepared for administration, they may be combined with a pharmaceutically acceptable carrier, diluent or excipient to form a pharmaceutical formulation, or unit dosage form. The total active ingredients in such formulations include from 0.1 to 99.9% by weight of the formulation. A "pharmaceutically acceptable" is a carrier, diluent, excipient, and/or salt that is compatible with the other ingredients of the formulation, and not deleterious to the recipient thereof. The active ingredient for administration may be present as a powder or as granules; as a solution, a suspension or an emulsion.

Pharmaceutical formulations containing the therapeutic agents of the invention can be prepared by procedures known in the art using well known and readily available ingredients. The therapeutic agents of the invention can also be formulated as solutions appropriate for parenteral administration, for instance by intramuscular, subcutaneous or intravenous routes.

The pharmaceutical formulations of the therapeutic agents of the invention can also take the form of an aqueous or anhydrous solution or dispersion, or alternatively the form of an emulsion or suspension.

Thus, the therapeutic agent may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

It will be appreciated that the unit content of active ingredient or ingredients contained in an individual aerosol dose of each dosage form need not in itself constitute an effective amount for treating the particular indication or disease since the necessary effective amount can be reached by administration of a plurality of dosage units. Moreover, the effective amount may be achieved using less than the dose in the dosage form, either individually, or in a series of administrations.

The pharmaceutical formulations of the present invention may include, as optional ingredients, pharmaceutically acceptable carriers, diluents, solubilizing or emulsifying agents, and salts of the type that are well-known in the art. Specific non-limiting examples of the carriers and/or diluents that are useful in the pharmaceutical formulations of the present invention include water and physiologically acceptable buffered saline solutions such as phosphate buffered saline solutions pH 7.0-8.0 and water.

EXAMPLE 1

Production of NES Loops

Nxf1 Export Sequence (NES) loops were prepared and inserted into shRNA and microRNA molecules, and tested for export by cells. In certain embodiments the NES loops made were "NES-long" and "NES-short" as indicated below (and shown in FIGS. 6, 7A and 7B):

```
NES-long #1:
                                          (SEQ ID NO: 1)
5'-ACACAGGAAG GGGAAUAUCA CACUCUGGGG AU-3'

NES-long #2:
                                          (SEQ ID NO: 3)
5'-ACACAGGAAG GGGAAUAUCA CACUCUGGGA U-3'

NES-short:
                                          (SEQ ID NO: 2)
5'-ACACAGGAAG GGGAU-3'
```

The complete loop region, not including any of the duplexing stem, is two nucleotides shorter than the sequences indicated above, as the 5'-A and the U-3' bind together close the loop region. The complete loop regions, not including these nucleotides are the following:

```
NES-long #1:
                                          (SEQ ID NO: 4)
5'-CACAGGAAGG GGAAUAUCAC ACUCUGGGGA-3'

NES-long #2:
                                          (SEQ ID NO: 5)
5'-CACAGGAAGG GGAAUAUCAC ACUCUGGGA -3'

NES-short:
                                          (SEQ ID NO: 6)
5'-CACAGGAAGG GGA-3'
```

Figure 6:
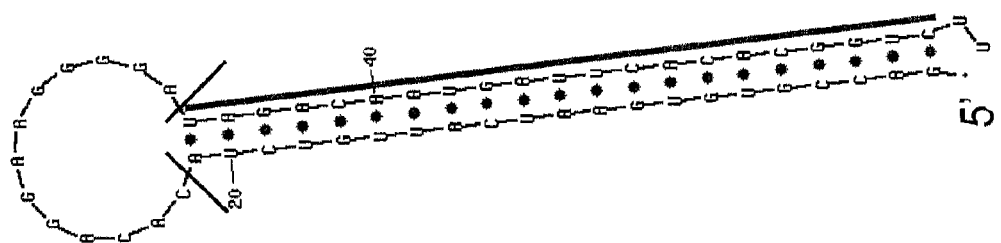
FIG. 6. sh2.4 L1 loop short (also called "NES-short"). Long line parallel to duplex indicates antisense guide strand. Hashes represent boundaries of the L1 loop short. Terminal Us are predicted products of RNA pol III termination. The full-length exemplary shRNA shown is SEQ ID NO:7.
Figure 7A:
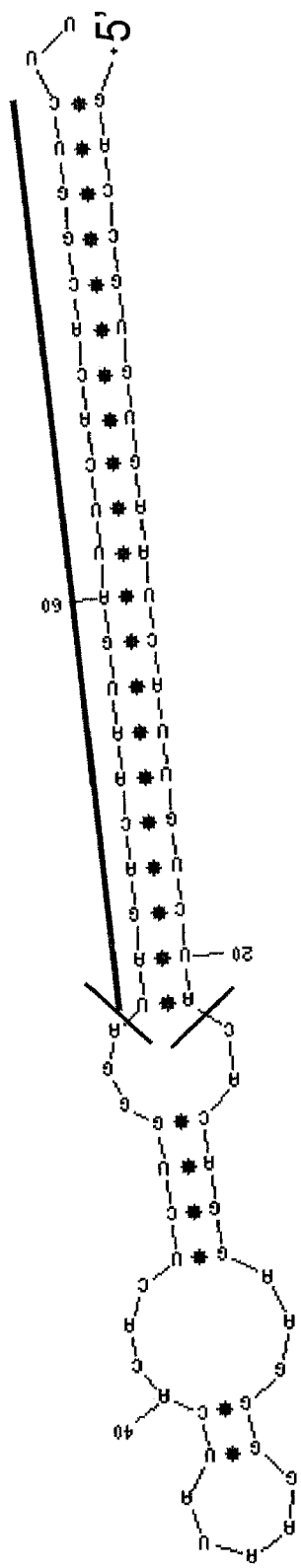
FIG. 7A. sh2.4 L1 loop long #1 (also called "NES-long"). Long line parallel to duplex indicates antisense guide strand. Hashes represent boundaries of the L1 loop long. Terminal Us are predicted products of RNA pol III termination. (−44.85 kcal·mole-1) The full-length exemplary shRNA shown is SEQ ID NO:8.
Figure 7B:
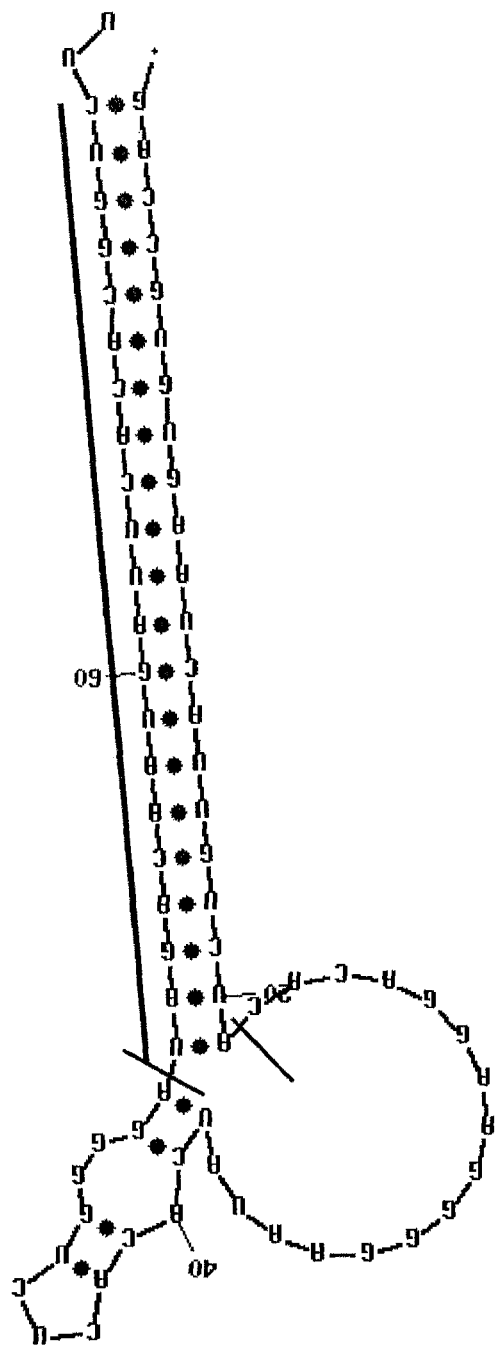
FIG. 7B. sh2.4 L1 loop long #2 (also called "NES-long"). Long line parallel to duplex indicates antisense guide strand. Hashes represent boundaries of the L1 loop long. Terminal Us are predicted products of RNA pol III termination. (−38.72 kcal·mole-1) The full-length exemplary shRNA shown is SEQ ID NO:9.

NES-long are superior to NES-short. Further, NES-long #2 is more thermodynamically stable than NES-long #1. As indicated in FIGS. 6, 7A and 7B, the duplex and overhang regions of the shRNAs were identical. Thus, the difference in biological activity is due to the different loop regions. In contrast to other RNAi molecules, which do not contain these types of loops and are exported via Exportin-V, the shRNAs containing NES loops were exported via nxf-1.

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A method of reducing the expression of a gene product in a mammalian cell, comprising contacting the mammalian cell with an isolated nucleic acid molecule comprising
   a first portion, wherein the first portion is no more than 30 nucleotides in length;
   a second portion, wherein the second portion has a sequence that is complementary to the first portion; and
   a loop portion consisting of 12 to 50 nucleotides, wherein the loop portion comprises between 12 and 32 nucleotides of SEQ ID NO:1, and is a sequence designed to circumvent exportin-5 mediated export;
   wherein the first portion and the second portion are operably linked by means of the loop portion to form a hairpin structure comprising a duplex structure that is 10 to 29 base pairs in length and a loop structure.

2. The method of claim 1, wherein the loop portion comprises between 12 and 32 contiguous nucleotides of SEQ ID NO:1.

3. The method of claim 1, wherein the loop portion is about 20 to 40 nucleotides long.

4. The method of claim 1, wherein the loop portion is about 25 to 35 nucleotides long.

5. The method of claim 1, wherein the loop portion is a 31 or 32 nucleotide L1 motif.

6. The method of claim 1, wherein the duplex contains from 19 to 25 base pairs.

7. The method of claim 1, wherein the molecule is a short hairpin RNA (shRNA).

8. The method of claim 1, wherein the loop portion consists of SEQ ID NO:5.

9. The method claim 1, wherein the duplex contains from 19 to 25 base pairs.

10. A method of reducing the expression of a gene product in a mammalian cell, comprising contacting the mammalian cell with an expression cassette comprising a sequence encoding a nucleic acid molecule comprising:
    a promoter;
    a first portion, wherein the first portion is no more than 30 nucleotides in length;
    a second portion, wherein the second portion has a sequence that is complementary to the first portion; and
    a loop portion consisting of 12 to 50 nucleotides, wherein the loop portion is a sequence designed to circumvent exportin-5 mediated export;
    wherein the first portion and the second portion are operably linked by means of the loop portion to form a hairpin structure comprising a duplex structure and a loop structure.

11. The method of claim 10, wherein the expression cassette is contained in a vector.

12. The method of claim 10, wherein the loop portion comprises between 12 and 32 nucleotides of SEQ ID NO:1.

13. The method of claim 10, wherein the loop portion comprises between 12 and 32 contiguous nucleotides of SEQ ID NO:1.

14. The method of claim 10, wherein the loop portion is about 20 to 40 nucleotides long.

15. The method of claim 10, wherein the loop portion is about 25 to 35 nucleotides long.

16. The method of claim 10, wherein the loop portion is a 31 or 32 nucleotide L1 motif.

17. The method claim 10, wherein the duplex contains from 19 to 25 base pairs.

18. The method claim 10, wherein the molecule is a short hairpin RNA (shRNA).

19. The method of claim 10, wherein the loop portion consists of SEQ ID NO:5.

20. A method of modifying a mammalian cell, comprising contacting the mammalian cell with an isolated nucleic acid molecule comprising
    a first portion, wherein the first portion is no more than 30 nucleotides in length;
    a second portion, wherein the second portion has a sequence that is complementary to the first portion; and
    a loop portion consisting of 12 to 50 nucleotides, wherein the loop portion comprises between 12 and 32 nucleotides of SEQ ID NO:1, and is a sequence designed to circumvent exportin-5 mediated export;
    wherein the first portion and the second portion are operably linked by means of the loop portion to form a hairpin structure comprising a duplex structure that is 10 to 29 base pairs in length and a loop structure.

21. The method of claim 20, wherein the modifying comprises transforming or transducing the mammalian cell.

22. The method of claim 20, wherein the nucleic acid further comprises an AAV vector.

23. The method of claim 1, wherein the nucleic acid further comprises an AAV vector.

24. The method of claim 10, wherein the nucleic acid further comprises an AAV vector.

* * * * *

SEQUENCE LISTING

```
<160> NUMBER OF SEQ ID NOS: 9

<210> SEQ ID NO 1
<211> LENGTH: 32
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
acacaggaag gggaauauca cacucugggg au                                     32

<210> SEQ ID NO 2
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
acacaggaag gggau                                                        15

<210> SEQ ID NO 3
<211> LENGTH: 31
<212> TYPE: RNA
<213> ORGANISM: Artificial Sequence
<220> FEATURE:
<223> OTHER INFORMATION: Description of Artificial Sequence: Synthetic
```

-continued oligonucleotide

<400> SEQUENCE: 3
acacaggaag gggaauauca cacucuggga u                              31

<210> SEQ ID NO 4
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
cacaggaagg ggaauaucac acucugggga                                30

<210> SEQ ID NO 5
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
cacaggaagg ggaauaucac acucuggga                                 29

<210> SEQ ID NO 6
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
cacaggaagg gga                                                  13

<210> SEQ ID NO 7
<211> LENGTH: 57
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
gaccguguga aucauugucu acacaggaag gggauagaca augauucaca cggucuu    57

<210> SEQ ID NO 8
<211> LENGTH: 73
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
gaccguguga aucauugucu acacaggaag gggaauauca cacucuggga uagacaauga   60
uucacacggu cuu                                                     73

<210> SEQ ID NO 9
<211> LENGTH: 74
<212> TYPE: RNA
<213> ORGANISM: Artificial Sequence
<220> FEATURE:

```
<223> OTHER INFORMATION: Description of Artificial Sequence: Synthetic
      oligonucleotide

<400> SEQUENCE: 9
gaccguguga aucauugucu acacaggaag gggaauauca cacucugggg auagacaaug      60
auucacacgg ucuu                                                       74
```